US012773133B2

(12) United States Patent
Yasukawa et al.

(10) Patent No.: US 12,773,133 B2
(45) Date of Patent: Oct. 27, 2026

(54) INFORMATION PROCESSING APPARATUS, INFORMATION PROCESSING METHOD, AND NON-TRANSITORY COMPUTER READABLE MEDIUM

(71) Applicants: NEC CORPORATION, Tokyo (JP); National University Corporation Tokyo Medical and Dental University, Tokyo (JP)

(72) Inventors: Makoto Yasukawa, Tokyo (JP); Shuhei Noyori, Tokyo (JP); Akimoto Nimura, Tokyo (JP); Koji Fujita, Tokyo (JP); Takuya Ibara, Tokyo (JP)

(73) Assignees: NEC CORPORATION, Tokyo (JP); National University Corporation Tokyo and Dental University, Tokyo (JP)

( * ) Notice: Subject to any disclaimer, the term of this patent is extended or adjusted under 35 U.S.C. 154(b) by 350 days.

(21) Appl. No.: 18/396,312

(22) Filed: Dec. 26, 2023

(65) Prior Publication Data

US 2024/0206769 A1 Jun. 27, 2024

(30) Foreign Application Priority Data

Dec. 26, 2022 (JP) ................................ 2022-208525

(51) Int. Cl.
*A61B 5/00* (2006.01)
*A61B 5/113* (2006.01)
(Continued)

(52) U.S. Cl.
CPC ................ *A61B 5/113* (2013.01); *G06T 7/11* (2017.01); *G06V 10/25* (2022.01); *G06V 10/44* (2022.01); *G06V 10/761* (2022.01); *G06V 40/20* (2022.01)

(58) Field of Classification Search
CPC ..... A61B 5/113; A61B 5/0816; A61B 5/7267; G06T 7/11; G06V 10/25; G06V 10/44; G06V 10/761; G06V 40/20
See application file for complete search history.

(56) References Cited

U.S. PATENT DOCUMENTS 5,749,365 A 5/1998 Magill
9,750,429 B1 9/2017 Sackner et al.
(Continued)

FOREIGN PATENT DOCUMENTS

JP H07-500748 A 1/1995
JP 2005-003366 A 1/2005
(Continued)

OTHER PUBLICATIONS

Notice of Reasons for Refusal issued Sep. 8, 2026, in Japanese Patent Application No. 2022-208525.

*Primary Examiner* — May A Abouelela
(74) *Attorney, Agent, or Firm* — Sughrue Mion, PLLC

(57) ABSTRACT

An information processing apparatus and the like capable of calculating a respiratory feature amount necessary for evaluating a breathing motor function of a subject is provided. The information processing apparatus inputs time-series distance image data acquired by measuring a distance from the subject during a breathing exercise and division position data indicating a position at which a chest region and an abdominal region of the subject are divided in the time-series distance image data. The information processing apparatus calculates a standard deviation image indicating a standard deviation of values for each pixel in a distance image indicated by the time-series distance image data. The information processing apparatus calculates a respiratory feature amount indicating a feature of breathing of the subject, based on a divided standard deviation image
(Continued)

acquired by dividing the standard deviation image for each divided region being divided at a position indicated by the division position data.

20 Claims, 22 Drawing Sheets

(51) Int. Cl.

| | |
|---|---|
| ***G06T 7/11*** | (2017.01) |
| ***G06V 10/25*** | (2022.01) |
| ***G06V 10/44*** | (2022.01) |
| ***G06V 10/74*** | (2022.01) |
| ***G06V 40/20*** | (2022.01) |

(56) References Cited

U.S. PATENT DOCUMENTS 11,589,776 B2* 2/2023 Choi .................... A61B 5/0033
2002/0032386 A1 3/2002 Sackner et al.
2003/0135127 A1 7/2003 Sackner et al.
2006/0279428 A1 12/2006 Sato et al.
2011/0087115 A1 4/2011 Sackner et al.
2015/0094606 A1* 4/2015 Mestha ................ A61B 5/7282 600/534
2015/0265187 A1* 9/2015 Bernal ................. A61B 5/1128 600/534
2016/0235344 A1* 8/2016 Auerbach ............ A61B 5/0077
2018/0049669 A1* 2/2018 Vu ....................... A61B 5/0507
2018/0117359 A1* 5/2018 Hale .................... A61N 5/1037
2019/0307367 A1* 10/2019 Senegas ............. G01R 33/5673
2020/0121256 A1* 4/2020 Mcduff .................... G06N 3/09
2020/0138292 A1* 5/2020 Choi ...................... A61B 5/091
2020/0138336 A1* 5/2020 Shim .................... A61B 5/1135
2020/0187827 A1* 6/2020 Addison .............. A61B 5/0816
2020/0234485 A1* 7/2020 Moghari .............. A61B 5/0044
2020/0260052 A1* 8/2020 Hutchinson ............ A61B 5/113
2020/0264273 A1 8/2020 Xie et al.
2020/0341745 A1* 10/2020 Verbeke ............... A61B 5/6893
2021/0169375 A1* 6/2021 Slepian .................... A61B 5/05
2021/0188291 A1* 6/2021 el Kaliouby ........... G16H 20/70
2021/0235992 A1* 8/2021 Addison ............ A61B 5/02427
2022/0233096 A1* 7/2022 Smit ...................... A61B 5/091
2022/0240790 A1* 8/2022 Smit .................... A61B 5/1135
2022/0313112 A1* 10/2022 Wolfe .................. A61B 5/4806
2022/0322966 A1 10/2022 Shin et al.
2023/0000429 A1* 1/2023 Shin .......................... A61F 5/56
2023/0005154 A1* 1/2023 Garcia I Tormo ........ G06T 7/80
2023/0082016 A1* 3/2023 Montgomery ....... A61B 5/7425 600/529
2023/0112712 A1* 4/2023 Montgomery ....... A61B 5/0077 600/476
2023/0191053 A1* 6/2023 Wilkerson .......... A61M 16/022 128/202.22
2023/0248268 A1* 8/2023 Sa ........................ A61B 5/7285 600/534
2023/0308457 A1* 9/2023 Fredrickson ........ H04L 63/1416
2023/0329636 A1* 10/2023 Ramp .................... G16H 40/63
2023/0364368 A1* 11/2023 Lyon .................... A61B 5/0205
2023/0397880 A1* 12/2023 Holley ................. A61B 5/7275
2024/0005523 A1* 1/2024 Wiesner ................ G06T 7/0012
2024/0065663 A1* 2/2024 Menser ..................... G06T 7/20
2024/0090795 A1* 3/2024 Heng ........................ G06T 7/20
2024/0268711 A1* 8/2024 Gwak .................. A61B 5/0816
2024/0269513 A1* 8/2024 Rahman ................. G16H 50/20
2024/0320834 A1* 9/2024 Wang .................... G06T 7/0012
2025/0025052 A1* 1/2025 Taebi ................... A61B 5/1128
2025/0131771 A1* 4/2025 Gajbhiye .................. G06T 7/20
2025/0177784 A1* 6/2025 Berlinger ............. A61N 5/1068

FOREIGN PATENT DOCUMENTS

JP 2005-218507 A 8/2005
JP 2011-136182 A 7/2011
JP 2011-206148 A 10/2011
JP 2019-063200 A 4/2019
JP 2020-134513 A 8/2020
JP 2020-185020 A 11/2020
WO 2020/226182 A1 11/2020

* cited by examiner

30SL

17a

| MOVEMENT VIEWED FROM SIDE | | MOVING PART | | | |
|---|---|---|---|---|---|
| | | ONLY CHEST | ONLY ABDOMEN | CHEST/ ABDOMEN | ABSENCE |
| WARP OF BACK | PRE-SENCE | | | | |
| | AB-SENCE | | | | |

Fig. 10

17b

| MOVEMENT VIEWED FROM FRONT | | MOVING PART | | | |
|---|---|---|---|---|---|
| | | ONLY RIGHT FLANK | ONLY LEFT FLANK | RIGHT/LEFT FLANK | ABSENCE |
| SHOULDER RISE | PRE-SENCE | | | | |
| | AB-SENCE | | | | |

Fig. 11

INFORMATION PROCESSING APPARATUS, INFORMATION PROCESSING METHOD, AND NON-TRANSITORY COMPUTER READABLE MEDIUM

INCORPORATION BY REFERENCE

This application is based upon and claims the benefit of priority from Japanese patent application No. 2022-208525, filed on Dec. 26, 2022, the disclosure of which is incorporated herein in its entirety by reference.

TECHNICAL FIELD

The present disclosure relates to an information processing apparatus, an information processing method, and a program.

BACKGROUND ART

For improving and maintaining a health condition, it is desirable to breathe by a correct breathing method. In order to confirm whether breathing is performed by the correct breathing method, movements of a chest portion and an abdomen portion are detected.

In this regard, International Patent Publication No. WO2020/226182 discloses a breathing state detection apparatus including a respiratory accessory muscle region detection device, a moving image processing device, and a breathing motion determination device. The respiratory accessory muscle region detection device extracts a respiratory accessory muscle existence region in which a respiratory accessory muscle exists from a moving image including a neck portion of a person. The moving image processing device extracts a morphological feature in the respiratory accessory muscle existence region. The breathing motion determination device determines recruitment of respiratory accessory muscles from time-series fluctuation of the morphological feature.

However, although the technique described in International Patent Publication No. WO2020/226182 can determine recruitment of respiratory accessory muscles around the neck portion and shoulder, it is not possible to recognize movements of other parts, and it is not possible to recognize a characteristic of movement of the chest and abdomen portion, which is important in musculoskeletal disorders. Therefore, with the technique described in International Patent Publication No. WO2020/226182, it is not possible to calculate a feature amount necessary for evaluation of a breathing motor function.

SUMMARY

In order to solve the above-described problem, an example object of the present disclosure is to provide an information processing apparatus, an information processing method, a program, and the like that are capable of calculating a respiratory feature amount necessary for evaluating a breathing motor function of a subject.

In a first example aspect according to the present disclosure, an information processing apparatus includes: an input unit configured to input time-series distance image data acquired by measuring a distance from a subject during a breathing exercise and division position data indicating a position that divides a chest region and an abdominal region of the subject in the time-series distance image data; a deviation calculation unit configured to calculate a standard deviation image indicating a standard deviation of values for each pixel in a distance image indicated by the time-series distance image data; and a feature amount calculation unit configured to calculate a respiratory feature amount indicating a feature of breathing of the subject, based on a divided standard deviation image acquired by dividing the standard deviation image for each divided region that is divided at a position indicated by the division position data.

In a second example aspect according to the present disclosure, an information processing method includes: inputting time-series distance image data acquired by measuring a distance from a subject during a breathing exercise and division position data indicating a position that divides a chest region and an abdominal region of the subject in the time-series distance image data; calculating a standard deviation image indicating a standard deviation of values for each pixel in a distance image indicated by the time-series distance image data; and calculating a respiratory feature amount indicating a feature of breathing of the subject, based on a divided standard deviation image acquired by dividing the standard deviation image for each divided region that is divided at a position indicated by the division position data.

In a third example aspect according to the present disclosure, a program is a program causing a computer to execute information processing of: inputting time-series distance image data acquired by measuring a distance from a subject during a breathing exercise, and division position data indicating a position that divides a chest region and an abdominal region of the subject in the time-series distance image data; calculating a standard deviation image indicating a standard deviation of values for each pixel in a distance image indicated by the time-series distance image data; and calculating a respiratory feature amount indicating a feature of breathing of the subject, based on a divided standard deviation image acquired by dividing the standard deviation image for each division region that is divided at a position indicated by the division position data.

BRIEF DESCRIPTION OF DRAWINGS

The above and other aspects, features, and advantages of the present disclosure will become more apparent from the following description of certain example embodiments when taken in conjunction with the accompanying drawings, in which:

FIG. 10 is a diagram illustrating an example of an evaluation label according to the present disclosure, the evaluation label being acquired by evaluating a subject when viewed from a side;

FIG. 11 is a diagram illustrating an example of an evaluation label according to the present disclosure, the evaluation label being acquired by evaluating a subject when viewed from a front;

EXAMPLE EMBODIMENT

Figure 1:
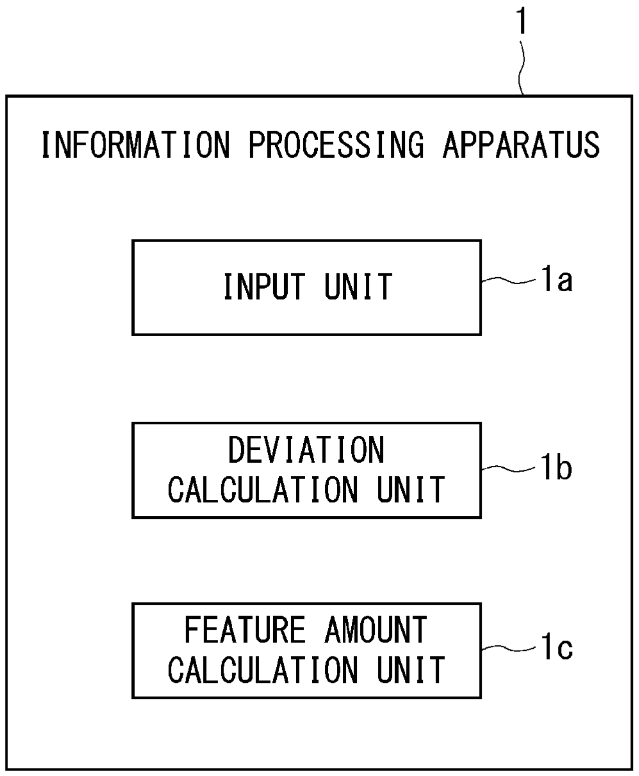
FIG. 1 is a block diagram illustrating a configuration example of an information processing apparatus according to the present disclosure.

Hereinafter, example embodiments will be explained with reference to the drawings. For clarity of explanation, the following description and the drawings are omitted and simplified as appropriate. In the drawings, the same elements are denoted by the same reference numerals, and redundant explanations are omitted as necessary.

First Example Embodiment

A configuration of an information processing apparatus 1 will be described in detail with reference to FIG. 1. FIG. 1 is a block diagram illustrating a configuration example of an information processing apparatus 1 according to the present disclosure. As illustrated in FIG. 1, the information processing apparatus 1 may include an input unit 1*a*, a deviation calculation unit 1*b*, and a feature amount calculation unit 1*c*, and may be used, for example, during an examination of a breathing state or during breathing training. Note that the examination of the breathing state may include an evaluation of the breathing state.

In order to improve and maintain a health condition, it is desirable to perform breathing with a correct breathing method, and in order to perform the correct breathing, it is desirable to continuously perform correct breathing training based on a guidance of a training instructor such as a doctor or a therapist (hereinafter, simply referred to as "instructor"). For example, breathing training with the correct breathing method may improve health conditions such as a physical function, such as a low back pain, and a mental status.

Herein, in the breathing training, it is considered that an effect of the training is better by the subject breathing in such a way that anteroposterior movements of a chest portion and an abdomen portion are synchronized with each other ("synchronization between the chest portion and the abdomen portion"). Furthermore, it is considered that the training effect is better by the subject breathing in such a way as to satisfy that ribs are sufficiently internally rotated when exhaling (at exhalation) (i.e., a width of the chest portion in a left-right direction becomes sufficiently small during exhalation; "internal rotation of ribs"). However, since it is difficult for the subject himself/herself to confirm the above, i.e., it is difficult for the subject to recognize his/her own breathing state, a system capable of accurately recognizing the breathing state is required. For this purpose, it is required to calculate a respiratory feature amount that accurately represents a feature of breathing of the subject.

In order to enable such calculation, the information processing apparatus 1 is used. Components of the information processing apparatus 1 will be explained.

The input unit 1*a* inputs time-series distance image data acquired by measuring a distance from a subject during a breathing exercise and division position data indicating a position at which a chest region and an abdominal region of the subject are divided in the time-series distance image data. Herein, the subject is a target person of calculation of the above-described respiratory feature amount, such as a person who performs breathing training. During a breathing exercise refers to the fact that the subject is in breathing, and may be defined as being, for example, in deep breathing or being quiet breathing. Note that the time-series distance image data may also be referred to as distance image series data.

The apparatus being an input source of the time-series distance image data may adopt various types of sensors capable of measuring a distance to an object, or may adopt a server or the like that stores distance image data acquired from the sensors. The sensor may be, for example, a three-dimensional camera. Examples of the three-dimensional camera include a depth sensor, Light Detection and Ranging (LiDAR), a stereo camera, and the like. Of course, the sensor can also be a depth sensor that is not a category of the three-dimensional camera. The sensor may measure a distance to an object by, for example, a Time of Flight (ToF) method, and the distance measurement method thereof is not limited.

A distance image indicated by the time-series distance image data to be input can be an image in which a distance value as a pixel value is stored in a pixel group associated to a measurement range for each measurement timing (each time). Of course, the distance image may adopt various formats in which the distance value at each time is stored in association with each position (coordinates) of a measurement mesh in the measurement range.

Therefore, the distance image may be a plurality of images associated with each time for each measurement timing, but may be included as information in such a way that a time, a position, and a distance value can be implicitly or explicitly associated with each other. The format of the time-series distance image data to be input is not limited as long as the time, the position, and the distance value can be implicitly or explicitly associated with each other. Of course, the above-mentioned time can also be a time from the start of the measurement.

Hereinafter, with respect to "images" such as a distance image and a standard deviation image, basically, a value of an optional position in the image is expressed as a value of a pixel associated to the position, i.e., a pixel value of the position.

The division position data are data indicating a position at which the chest region and the abdominal region of the subject are divided in the time-series distance image data. Therefore, the division position data may include a line that can represent a straight line or a curve line, or data of a position (pixel position or coordinate position) of one or a plurality of points, as a position for dividing the region.

The division position data may be data acquired together with time-series distance image data by the sensor. However, the division position data may be data acquired by performing image analysis on time-series distance image data, or may be data acquired by a sensor different from a sensor that acquires time-series distance image data.

Further, the division position data may include not only a position at which the chest region and the abdominal region of the subject are divided but also other region division positions. Examples of the other region division position include one or a plurality of positions among a position for dividing a left-side region, which is a region on a left side toward a front of the subject, and a right-side region, which is a region on a right side toward the front of the subject, a position for dividing the abdominal region and a waist region, and a position for dividing the chest region and a shoulder region.

The deviation calculation unit 1*b* calculates a standard deviation image indicating a standard deviation of values (pixel values) for each pixel in a distance image indicated by the time-series distance image data. Herein, an average value of pixel values (distance values) of a certain pixel for a period indicated by time-series distance image data is acquired, whereby the standard deviation of the pixel can be calculated as a value indicating a degree of variation from the average value. In other words, the standard deviation of a certain pixel becomes a standard deviation of the pixel value (distance value) in the above-described period, and the number of the standard deviation images calculated by the deviation calculation unit 1*b* can be one for the time-series distance image data.

Of course, it is also possible to adopt a configuration in which the deviation calculation unit 1*b* calculates the standard deviation image at every predetermined time period, and adopt a configuration in which the feature amount calculation unit 1*c* in a subsequent stage calculates a respiratory feature amount at every predetermined time period or a configuration in which the respiratory feature amount in the above-described period is calculated. However, in the present example embodiment, the second example embodiment to be described later, and the like, only an example in which one standard deviation image is calculated by the deviation calculation unit 1*b* will be explained for the sake of simplification of explanation.

As described above, the standard deviation image can be calculated by acquiring an average value of the values in the above-described time period for each pixel for all the pixels of the distance image and acquiring a standard deviation value that is a degree of variation from the average value for each pixel. The standard deviation image can be an image in which the standard deviation value of each pixel acquired in this way is arranged in each associated pixel of the original distance image.

The standard deviation image thus calculated can express explicitly how much the subject is moving during a breathing exercise, which location is moving a lot, i.e., which position pixel is changing a lot, and the like. In fact, a person to be a subject will repeatedly expand and contract at a part called a flank portion, for example, during a breathing exercise, and therefore, the standard deviation image can represent expansion movement (expansion and contraction movement) of a flank region that is a region of the flank portion, for example.

The feature amount calculation unit 1*c* calculates a respiratory feature amount indicating a feature of breathing of the subject, based on a divided standard deviation image. The calculation of the respiratory feature amount may also be referred to as extraction of the respiratory feature amount. Further, since the respiratory feature amount is a feature amount indicating breathing movement of the subject, it can also be referred to as a movement feature amount.

The divided standard deviation image is an image acquired by dividing the above-described standard deviation image for each divided region, and the divided region refers to each region divided at a position indicated by the division position data. Therefore, in a case where there are many region division positions and a division position other than the division position of the chest region and the abdominal region is also applied, the number of divided standard deviation images is increased by that amount.

However, it is not necessary to calculate the respiratory feature amount from all the divided standard deviation images, and the respiratory feature amount may be calculated from at least a divided standard deviation image for a region that is a category of the chest region and a divided standard deviation image for a region that is a category of the abdominal region. For example, in a case where the division position data include a region division position between the abdominal region and the waist region and a region division position between the chest region and the shoulder region, any one or both of a divided standard deviation image of the waist region and a divided standard deviation image of the shoulder region may not be used for calculating the respiratory feature amount.

As described above, the information processing apparatus 1 according to the present example embodiment inputs the distance image series data during a breathing exercise and the division position data including the position at which the chest and abdomen portion is divided, and calculates the respiratory feature amount, based on the standard deviation image. As described above, the standard deviation image can explicitly express how much the subject is moving during the breathing exercise, which location is moving a lot, and the like.

In particular, the information processing apparatus 1 calculates the respiratory feature amount, based on the divided standard deviation image acquired by dividing the standard deviation image at the division position. Then, by using the divided standard deviation images of the regions including at least the chest region and the abdominal region, it is possible to calculate the respiratory feature amount taking into consideration the respiratory feature amount indicating a synchrony between the regions, the synchrony, and the like.

As described above, in the information processing apparatus 1, it is possible to calculate the respiratory feature amount indicating the feature of the breathing of the subject, based on at least the movement of the chest portion and the movement of the abdomen portion of the subject. In short, in the information processing apparatus 1, it is possible to calculate a respiratory feature amount necessary for evaluating a respiratory motor function of the subject.

Although not illustrated, the information processing apparatus 1 may also include an output unit that outputs the calculated respiratory feature amount. In addition to the respiratory feature amount, the output unit may output a standard deviation image and information indicating a division position, or a divided standard deviation image. An output destination by the output unit may be at least one of a display device provided in the information processing apparatus 1, a display device connected to the information processing apparatus 1, a storage device inside or outside the information processing apparatus 1, and a printing device connected to the information processing apparatus 1.

The information being output in this way can be used as information for supporting a breathing training. Therefore, the information processing apparatus 1 can be referred to as a breathing training support apparatus. The breathing training is also referred to as a breathing exercise practice.

Further, in the present example embodiment, a supine position can be adopted as a posture of the subject at a time of acquiring the distance image data and the division position data, but the present disclosure is not limited thereto, and may be carried out in a supine position, a sitting position, a standing position, a knee standing position, a supine position and a leg raising position, or the like. However, an installation location of the apparatus being an input source of the distance image data and the division position data, the various image processing described above, and the like may be changed as appropriate depending on the posture. The distance image data and the division position data may be acquired from the front or back of the subject in accordance with the posture of the subject, but the posture that can acquire the data from the front does not need to restrict the breathing of the subject.

The information processing apparatus 1 illustrated in FIG. 1 may be, for example, a computer such as a server or a personal computer, or may be an apparatus including dedicated hardware. Specifically, the information processing apparatus 1 may include a computer apparatus including hardware including, for example, one or more processors and one or more memories. At least a part of functions of the units in the information processing apparatus 1 may be achieved by one or more processors operating in accordance with a program read from one or more memories.

In other words, the information processing apparatus 1 may include a control unit (not illustrated) that controls the whole of the information processing apparatus. The control unit can be achieved by, for example, a central processing unit (CPU) or a graphics processing unit (GPU), a working memory, a non-volatile storage device storing a program, and the like. This program can be a program for causing the CPU or the GPU to execute the processing of the input unit 1*a*, the deviation calculation unit 1*b*, and the feature amount calculation unit 1*c*.

In addition, the information processing apparatus 1 may include a storage device that stores input data such as time-series distance image data, data in the middle of processing, a calculation result of a respiratory feature amount, and the like, and as the storage device, a storage device included in the control unit may be used, for example.

Further, the information processing apparatus 1 is not limited to an example configured as a single apparatus, and may be constructed as a plurality of apparatuses in which functions are distributed, i.e., as an information processing system, and a method of distribution thereof is not limited. In a case of constructing an information processing system in which functions are distributed among a plurality of apparatuses, each apparatus may be provided with a control unit, a communication unit, and as necessary, a storage unit, and the like, and the plurality of apparatuses may be connected as necessary by wireless or wired communication and the functions explained in the information processing apparatus 1 may be achieved in cooperation with each other.

Figure 2:
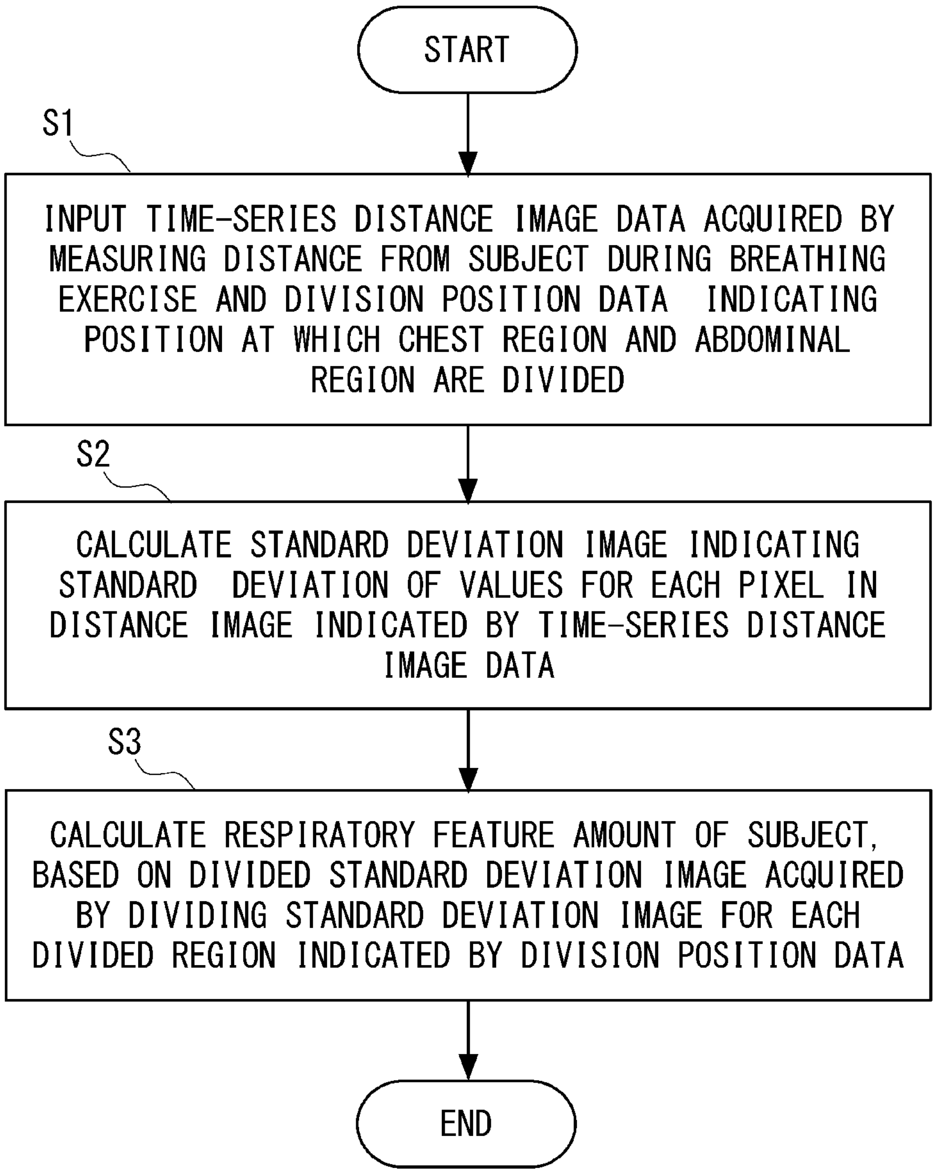
FIG. 2 is a flowchart for explaining an example of an information processing method according to the present disclosure.

Next, a processing example of the information processing apparatus 1 will be explained with reference to FIG. 2. FIG. 2 is a flowchart for explaining an example of an information processing method according to the present disclosure.

First, the information processing apparatus 1 inputs time-series distance image data acquired by measuring a distance from a subject during a breathing exercise, and division position data indicating a position at which a chest region and an abdominal region are divided (step S1). Next, the information processing apparatus 1 calculates a standard deviation image indicating a standard deviation of values for each pixel in a distance image indicate by the time-series distance image data (step S2).

Next, the information processing apparatus 1 calculates a respiratory feature amount of the subject, based on a divided standard deviation image acquired by dividing the standard deviation image for each divided region indicated by the division position data (step S3), and end the processing. Further, the respiratory feature amount can be output by providing the information processing apparatus 1 with an output unit.

As described above, according to the present example embodiment, it is possible to calculate the respiratory feature amount indicating a feature of the breathing of the subject, based on the movement of the chest and abdomen portion of the subject, and it is possible to calculate the respiratory feature amount necessary for evaluating a respiratory motion function of the subject.

This effect is supplementarily described. For example, in motor organ disorders such as a low back pain, abnormal breathing patterns occur, and therefore, movement examination and movement evaluation of the chest and abdomen portion during a breathing exercise are important. In addition, since the examination and evaluation by experts are generic, objective and quantitative examination technique and evaluation technique are required. In the present example embodiment, since the respiratory feature amount can be calculated based on the movement of each region divided by the chest (including a portion associated to the chest) region and the abdominal region, it can be said that the accuracy of such examination and evaluation can be improved.

In short, according to the present example embodiment, for example, the respiratory feature amount of the chest portion and the abdomen portion can be calculated by region, and the respiratory feature amount for musculoskeletal disorders can be also correctly defined. As described above, according to the present example embodiment, it is possible to improve the accuracy of the examination for capturing the movement of the chest portion and the abdomen portion, and it is also possible to improve precision of estimation of a breathing state of the subject. As a result, according to the present example embodiment, the accuracy of the evaluation of the breathing motor function can be improved, and the accuracy of guidance using the evaluation can also be improved, and effective guidance becomes possible.

In addition, in the present example embodiment, effective guidance can be performed by use of an instructor such as a therapist at a time of rehabilitation in a medical institution or breathing exercise practice in a healthcare service. Further, in the present example embodiment, by mounting the information processing apparatus 1 on a terminal device or the like to be used by a subject, the subject can receive remote instruction from the instructor or perform voluntary training while being at home.

Second Example Embodiment

Figure 3:
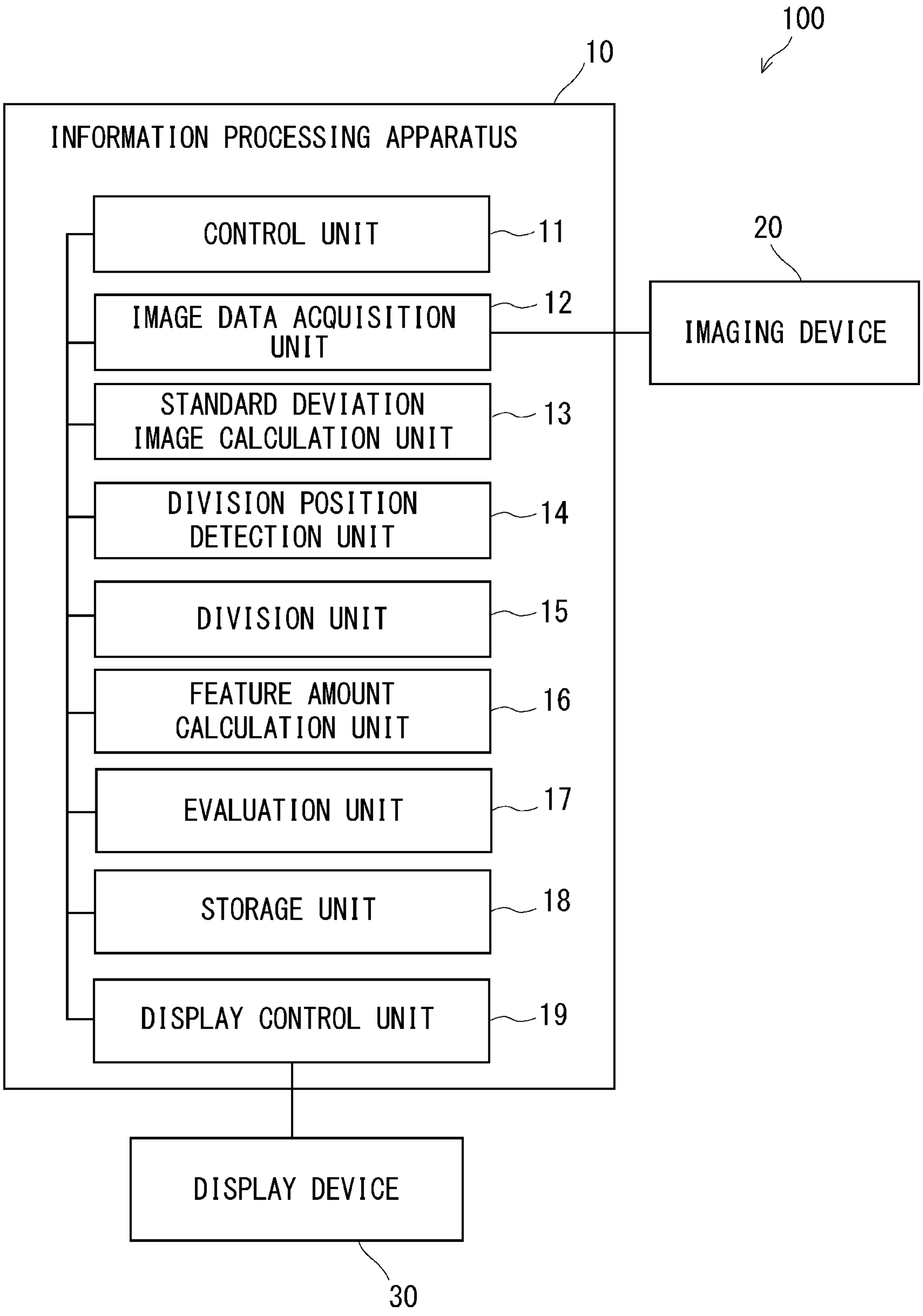
FIG. 3 is a block diagram illustrating a configuration example of a display system including an information processing apparatus according to the present disclosure.

Although the second example embodiment will be mainly explained with reference to FIGS. 3 to 20, various examples explained in the first example embodiment can be applied. First, a configuration example of an information display system (hereinafter, simply referred to as a display system) including an information processing apparatus according to the present example embodiment will be explained with reference to FIGS. 3 and 4. FIG. 3 is a block diagram illustrating a configuration example of a display system including an information processing apparatus according to the present disclosure, and FIG. 4 is a schematic side view illustrating an external appearance of the display system according to the present disclosure.

Figure 4:
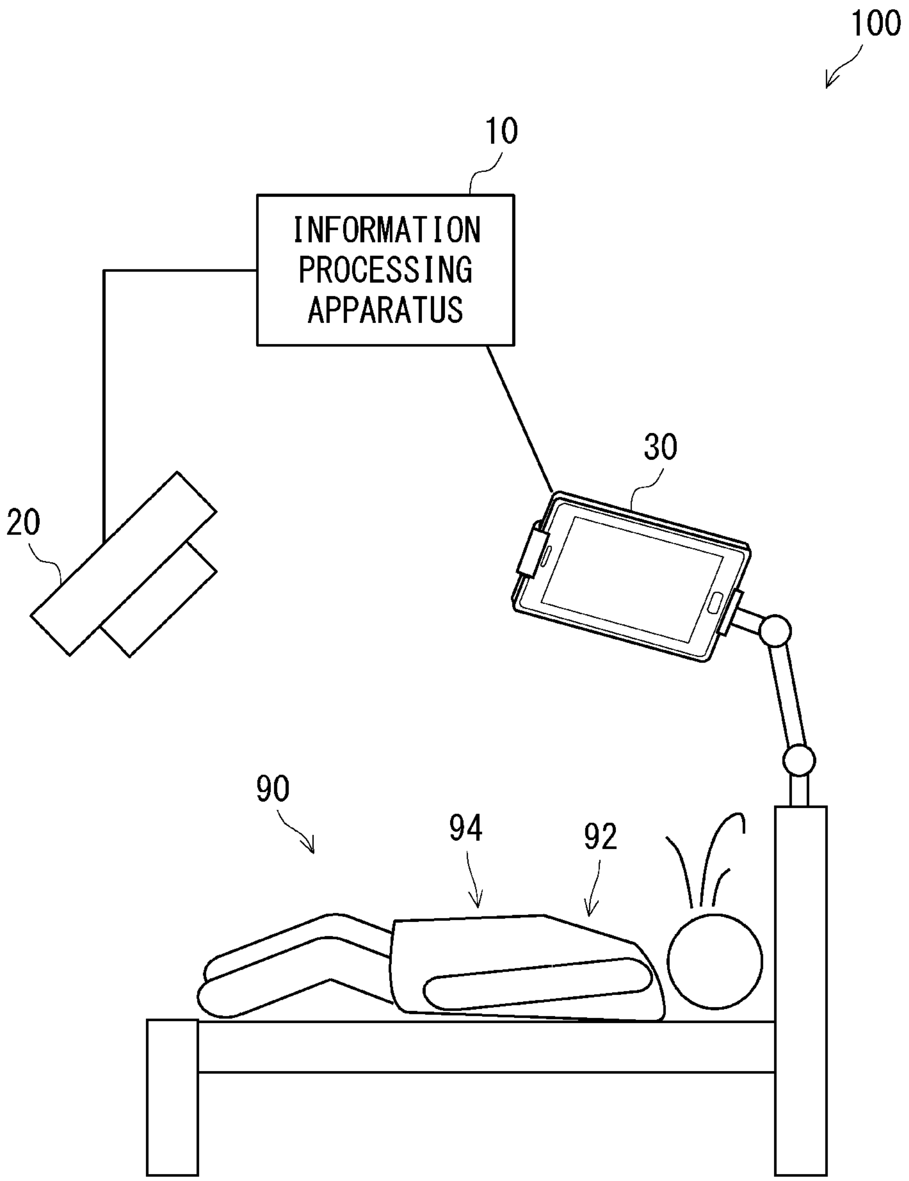
FIG. 4 is a schematic side view illustrating an appearance of the display system according to the present disclosure.

As illustrated in FIGS. 3 and 4, a display system 100 includes an information processing apparatus 10 that is an example of the information processing apparatus 1 illustrated in FIG. 1, at least one imaging device 20, and at least one display device 30. The information processing apparatus 10 is an example of the information processing apparatus 1 according to the first example embodiment, and is communicably connected to the imaging device 20 and the display device 30 via a wired or wireless network.

The display system 100 illustrated in FIG. 4 can be used when a subject 90 performs breathing training or examines a breathing state. As illustrated in FIG. 4, the subject 90 can perform breathing training and examination in a supine (supine position) state, but the posture of the subject 90 is not limited to the supine position. However, for the sake of simplicity of explanation, the following description will be given on the assumption that the subject 90 performs breathing training and examination in the supine position.

The imaging device 20 photographs the subject 90 to be target of breathing training or examination of a breathing state in order to acquire time-series distance image data acquired by measuring a distance from a subject during a breathing exercise. The imaging device 20 may be installed at a position where a chest portion 92 and an abdomen portion 94 of the subject 90 can be photographed. When the subject 90 performs breathing training or the like in the supine position, the imaging device 20 may be installed above the chest portion 92 and the abdomen portion 94 of the subject 90 as illustrated in FIG. 4, for example. In other words, the imaging device 20 can be installed at a position facing the subject 90 in the supine position.

Note that the subject 90 may perform breathing training or the like in a state of wearing clothes. In this case, the chest portion 92 is a portion associated to the chest portion of the subject 90 in a state of wearing clothes. Similarly, the abdomen portion 94 is a portion associated to the abdomen portion of the subject 90 in a state of wearing clothes. In particular, clothes, such as a compression shirt, that fits a body at least on the upper body of the subject 90 can improve accuracies of various processing because the distance measurement is more accurate.

The imaging device 20 may be any imaging device capable of measuring a distance to a target object, and may be, for example, a three-dimensional camera such as a depth sensor, LiDAR, or a stereo camera. The imaging device 20 may measure a distance to an object including at least the subject 90 by various distance measurement methods such as a ToF method. The imaging device 20 may also include a two-dimensional camera (e.g., an RGB camera, etc.).

The imaging device 20 generates time-series image data including at least the chest portion 92 and the abdomen portion 94 of the subject 90 as a photographing range by photographing the subject 90, and transmits the time-series image data to the information processing apparatus 10. In short, the time-series image data may indicate the chest portion 92 and abdomen portion 94 of the subject 90 and images (photographed images) around them. The photographed image may be a moving image or a still image captured at predetermined intervals. In the following description, the term “image” also means “image data indicating an image” as a processing target in information processing.

The time-series image data acquired by the imaging device 20 include data indicating time-series distance images, i.e., time-series distance image data. The time-series distance image data can be said to be data indicating a change in the position of the subject 90. In other words, the imaging device 20 can acquire time-series distance image data indicating the position of the subject 90 and the movement that is a change thereof, and transmit the time-series distance image data to the information processing apparatus 10. The distance image data may be, for example, three-dimensional image data represented by three-dimensional point cloud data.

Further, in the information processing apparatus 10, by using the time-series distance image data acquired by the imaging device 20, it is possible to detect a change in a position of the body including the chest portion 92 and the abdomen portion 94 of the subject 90, i.e., a movement of the body. For example, motion capture or the like can be achieved by using the imaging device 20. The position of the detection target may include a position in a vertical direction in the supine position, which is the position in the up-and-down direction in FIG. 4, and a position in a horizontal direction in the supine position.

Furthermore, skeletal data indicating a skeleton (joint) of the subject 90 that has been photographed may be generated by using the imaging device 20. The skeleton data are data indicating a position of the joint of the subject 90. The skeleton data can be used as an example of division position data indicating a position at which the chest region and the abdominal region of the subject are divided. The skeleton data can be acquired, for example, by the imaging device 20 or the information processing apparatus 10 recognizing the joint of the moving person. In the following description, an example in which processing of recognizing a joint, i.e., processing of detecting the joint is executed on a side of the information processing apparatus 10 will be explained, but a configuration that is executed on a side of the imaging device 20 may be adopted.

Further, as described above, the image data acquired by the imaging device 20 include the distance image data, but may also include two-dimensional image data such as an RGB image. Alternatively, the image data acquired by the imaging device 20 may be data indicating an image acquired by combining a two-dimensional image and a three-dimensional image. Accordingly, the distance image data may indicate position information regarding a position of the surface of the photographed subject 90 as three-dimensional coordinates by the three-dimensional point cloud data or the like. The two-dimensional image data or the three-dimensional image data may be used for acquiring the above-described skeleton data or may include the above-described skeleton data itself. The imaging device 20 transmits the generated image data to the information processing apparatus 10.

In the information processing apparatus 10, a standard deviation image can be calculated based on time-series distance image data in order to express a change in the position of the body including the chest portion 92 and the abdomen portion 94 of the subject 90. Further, in the information processing apparatus 10, the standard deviation image is divided based on the division position data, and the respiratory feature amount indicating the feature of the breathing of the subject can be calculated based on the image (divided standard deviation image) for each divided region as a result of the division. The calculation of the respiratory feature amount based on the time-series distance image data and the division position data will be described later as an explanation of each component of the information processing apparatus 10.

The display device 30 is arranged in such a way as to display an image at a position visible from the subject 90. The display device 30 includes, for example, a display for displaying an image. The display device 30 includes, for example, a Liquid Crystal Display (LCD), but is not limited thereto. The display device 30 may be achieved by an organic Electro-Luminescence (EL) display, a projector, or the like. The display device 30 may be, for example, a smartphone or a tablet terminal. Examples of contents displayed by the display device 30 will be described later.

Further, as illustrated in FIG. 4, the display device 30 may display an image for the subject 90 when being installed over the head of the subject 90. For example, the display device 30 may display an image for the subject 90 when the camera built in a display device 30 detects a face of the subject 90.

Further, in the display device 30, information can be displayed as information for the subject 90 or as information for the instructor, and display contents can be made different in consideration of clarity or the like depending on a target person of browsing. For example, when the display device 30 is a display device possessed by the instructor, information for the instructor can be displayed.

Although the following will be explained on the assumption that the display device 30 is used for the subject 90 to browse the information, the display device 30 may be used for the instructor to browse the information, or a plurality of display devices 30 for the subject 90 and the instructor may be provided in the display system 100.

Next, a specific configuration example of the information processing apparatus 10 will be explained. As illustrated in FIG. 3, the information processing apparatus 10 may include a control unit 11, an image data acquisition unit 12, a standard deviation image calculation unit 13, a division position detection unit 14, a division unit 15, a feature amount calculation unit 16, an evaluation unit 17, a storage unit 18, and a display control unit 19.

Control Unit 11

The control unit 11 is a part that controls the entire information processing apparatus 10, and may include a processor such as a CPU or a GPU, for example, and may include a program for control. The control unit 11 has a function as an arithmetic device that performs control processing, arithmetic processing, and the like, and controls the image data acquisition unit 12, the standard deviation image calculation unit 13, the division position detection unit 14, the division unit 15, the feature amount calculation unit 16, the evaluation unit 17, the storage unit 18, and the display control unit 19.

Image Data Acquisition Unit 12

The image data acquisition unit 12 may include an interface such as a communication interface for wired or wireless connection to the imaging device 20. Then, the image data acquisition unit 12 acquires image data acquired by photographing the subject 90 during a breathing exercise from the imaging device 20. The acquired image data including the time-series distance image data (hereinafter, also referred to as a distance image series) are data measured for one or a plurality of breathing cycles of the subject 90, whereby processing based on the data for the breathing cycles of the subject 90 is enabled. The image data acquisition unit 12 outputs at least time-series distance image data among the acquired image data to the standard deviation image calculation unit 13. Further, the image data acquisition unit 12 can output the acquired image data to the division position detection unit 14.

In particular, the image data to be acquired, including the distance image series, may be data measured while the subject 90 is breathing deep. As described above, during the breathing exercise as an acquisition target period of the distance image series indicates that the subject 90 is in breathing, and for example, the subject 90 may be in deep breathing.

Of course, during the breathing exercise may be during quiet breathing or a period of time during which the subject 90 is allowed to breathe freely, even not during the deep breathing. It can be said that the image data during deep breathing or during quiet breathing are beneficial in that the data are easier to compare the breathing movement of the subject 90 with those of other subjects than data in other cases, or the data are easier to identify a musculoskeletal disorder than data in other cases.

Standard Deviation Image Calculation Unit 13

The standard deviation image calculation unit 13 calculates a standard deviation image indicating a standard deviation of values for each pixel in a distance image indicated by time-series distance image data, and outputs the standard deviation image to the division unit 15. As described above, the standard deviation of a certain pixel can refer to the degree of variation in value (distance value) of the pixel existing in time series with respect to the period indicated by the time-series distance image data, i.e., the period indicated by the distance image series. Therefore, the fact that the standard deviation of a certain pixel is larger than the standard deviation of another pixel indicates that the position of the body of the subject 90 associated to the certain pixel has moved more than the other positions in the above-described period.

Division Position Detection Unit 14

The division position detection unit 14 receives image data from the image data acquisition unit 12 as data to be a detection source of division position data, detects the division position data from the image data, and outputs the division position data to the division unit 15. This detection example will be described later. In the configuration example of FIG. 3, the image data acquisition unit 12 and the division position detection unit 14 input the division position data. However, it is also possible to provide a function of acquiring division position data on a side of the imaging device 20, and in this case, the information processing apparatus 10 may not include the division position detection unit 14, and the image data acquisition unit 12 may pass the division position data to the division unit 15.

The division position data are data indicating a position at which the chest region and the abdominal region of the subject 90 are divided in the time-series distance image data, and may include a line at which a straight line or a curve can be represented as a position at which the region is divided, or data of a position of one or a plurality of points. The chest region may refer to a region of the chest portion 92 and the abdominal region may refer to a region of the abdomen portion 94.

The division position data can be data acquired together with time-series distance image data by the imaging device 20, and in this case, the division position detection unit 14 can detect the division position data by extracting the division position data from the image data. Alternatively, the division position data may be data acquired by performing image analysis on time-series distance image data. In either case, the division position data can be acquired from the imaging device 20 as part of the image data as skeleton data or the like as described above. The division position data may be data acquired by a sensor different from the imaging device 20 that acquires time-series distance image data, and in this case, the division position detection unit 14 may acquire the data.

Further, the division position data may include not only a position at which the chest region and the abdominal region of the subject 90 are divided but also other division positions. Examples of the other region division position include one or a plurality of a position at which a left-side region and a right-side region of the subject 90 are divided, a position at which the abdominal region and a waist region are divided, a position at which the chest region and a shoulder region are divided, and a position at which the chest region, the shoulder region, and an arm region are divided.

Note that the division position data can also be used as follows. In other words, the division position data can be used in order to delete information of a region that is not required in future for the image data including the input distance image series. The division position data can be used in order to adjust a direction and a position of an intersection line of each plane for a sagittal plane, a frontal plane, and a transverse plane of the subject 90 in such a way as to be suitable for processing, with respect to the image data including the input distance image series.

Of course, at a time of acquiring image data such as a distance image series, it is also possible to devise in such a way that the subject 90 is in the correct position and orientation suitable for processing. The devisal may also include displaying, on the display device 30, an advice for correcting the position and the orientation of the subject 90, based on the division position data.

An outline of a detection example of the division position data from the image data by the division position detection unit 14 will be explained. The division position detection unit 14 detects the position of the joint of the subject 90, based on the image data acquired by the image data acquisition unit 12, and outputs the detection result to the division unit 15 as division position data. As described above, the division position data may be data indicating a position of the joint of the subject 90, and in this case, the division position data may be referred to as joint position data, and the division position detection unit 14 may be referred to as a joint position detection unit.

The joint position data can be acquired by performing image analysis on the two-dimensional image data captured by the two-dimensional camera included in the imaging device 20 or by performing image analysis on the distance image data captured by the imaging device 20. For example, a predetermined mark may be attached to a joint of the subject 90 for a joint that needs to be positioned in advance in the image analysis, and the predetermined mark may be detected. However, a method of acquiring the joint position data and a detection method for detecting the position of the joint are not limited to these, and various known techniques such as a motion capture technique can be used.

Note that various existing techniques can be used to detect the joint. The joint may be detected based on the distance image data, or may be detected based on RGB two-dimensional image data. Various detection algorithms to be used for the detection of the joint are distributed, but the number and the position to be detected differs depending on the detection algorithm, and therefore, the joint key point matching the purpose of use may be selected according to the detection algorithm to be used.

Further, although an example in which the division position data are joint position data indicating a position of the joint has been explained, the present disclosure is not limited thereto. For example, from the image data, the intersection line between the frontal plane and the sagittal plane of the subject 90 can be detected as the center line in the left-right direction of the body of the subject 90, and an edge of the shoulder portion can be detected. In this case, the dividing position data can include data in which the dividing position is a point indicated by a distance from the edge of the shoulder on the intersection line. The distance can be calculated based on the height of the subject 90 being input in advance.

Division Unit 15

The division unit 15 inputs the standard deviation image calculated by the standard deviation image calculation unit 13 and the division position data acquired as the detection result by the division position detection unit 14, for example, the joint position data acquired by measuring the position of the joint of the subject 90.

The division unit 15 can execute division processing including chest and abdominal division processing of dividing the standard deviation image into the chest region and the abdominal region of the subject 90 by using a differential value in a direction of an intersection line between the sagittal plane and the frontal plane of the subject 90 with respect to the standard deviation image. The differential value in the direction of the intersection line refers to a differential value in a direction parallel to the intersection line. The direction of the intersection line may be referred to as a height direction or a perpendicular direction of the subject 90. An example of the standard deviation image and an example of the division processing will be described later with a specific example.

The division processing to be executed by the division unit 15 may include any one or a plurality of left-right division processing, shoulder and chest division processing, abdomen-waist division processing, and arm division processing, in response to the position indicated by the division position data. In addition, the joint position data to be used in the left-right division processing, the shoulder and chest division processing, the abdomen and waist division processing, and the arm division processing can all be data acquired by measuring the position of the joint of the subject 90 at least at one time of a period associated to the distance image series. The left-right division processing, the shoulder and chest division processing, the abdomen and waist division processing, and the arm division processing may be executed before or after the chest and abdominal division processing, which is division processing of the chest region and the abdominal region.

The left-right division processing refers to processing of dividing the standard deviation image into a left-side region and a right-side region, based on, for example, a joint position indicated by the joint position data. The left-side region may refer to a region on a left side toward a front of the subject 90 (in a direction perpendicular to the sagittal plane of the subject 90), and the right-side region may refer to a region on a right side toward the front of the subject 90.

The shoulder and chest division processing refers to processing of dividing a standard deviation image into a shoulder region, which is a region of a shoulder portion of the subject 90, and the chest region, based on the joint position indicated by the joint position data, for example. The abdomen and waist division processing refers to processing of dividing a standard deviation image into the abdominal region and a waist region, which is a region of a waist portion of the subject, based on, for example, the joint position indicated by the joint position data. The arm division processing refers to processing of dividing a standard deviation image into an arm region and the chest region, or into the arm region, the chest region, and the shoulder region, based on, for example, the joint position indicated by the joint position data. At least one of the arm region and the waist region may be excluded by pretreatment.

The left-right division processing, the shoulder and chest division processing, the abdomen and waist division processing, and the arm division processing are basically processing of dividing the subject 90 into, respectively, for example, a sagittal plane near a sternum, a transverse plane near a clavicle, a transverse plane of an upper pelvis (upper ilium), and a plane extending from the vicinity of the clavicle to the side. Therefore, in any of these four types of division processing, it is assumed that the dividing result is not affected depending on the breathing movement of the subject 90, and therefore, it is sufficient that the position of the joint is measured at least at any time in the period associated to the distance image series.

However, the joint position data are not limited to data at one time, such as data at the first, intermediate, or last time of the distance image series, and may be average data of a period associated to the distance image series. In the example of the left-right division processing to be described later with reference to FIG. 16 and the like, since a result of the chest and abdominal division processing is used, as a result, it can be said that the joint position data are data measured for a period associated to the distance image series.

In all of the left-right division processing, the shoulder-chest division processing, the abdominal-waist part division processing, and the arm part division processing described above, the standard deviation image can be divided with the position of a predetermined joint indicated by the joint position data as a reference point. This reference point may be referred to as a joint key point. By setting the reference point to two or more points, i.e., by setting the position of the predetermined joint of two or more points as the reference point, it is possible to perform more accurate division processing.

The predetermined joint in the left-right division process may include, for example, a hip and a neck, or may include an upper end of the sternum. The predetermined joint in the shoulder and chest part split process may include, for example, left and right protruding portions of the clavicle. The predetermined joint in the abdominal-lumbar partial split process may include, for example, left and right protrusions on the upper portion of the pelvis. The predetermined joint in the arm part split process may include, for example, left and right ends and both sides of the clavicle. However, by using image data acquired by photographing the entire body of the subject 90 including left and right ankles and the neck or the head as a predetermined joint, more accurate left-right dividing processing can be performed. The present disclosure is not limited to this example, and it is possible to stably acquire the position of a predetermined joint by using image data acquired by photographing the entire body.

Feature Amount Calculation Unit 16

The feature amount calculation unit 16 calculates a respiratory feature amount indicating a characteristic of breathing of the subject 90, based on an image (hereinafter, referred to as a divided standard deviation image) of each divided region as a result of dividing the standard deviation image, based on the division position data. Note that the feature amount calculation unit 16 may also be referred to as a feature amount extraction unit because the respiratory feature amount is extracted from the divided standard deviation image or the like.

The divided standard deviation image is an image acquired by dividing the above-described standard deviation image for each divided region. When division positions other than the division position between the chest region and the abdominal region are also applied together, the number of the divided standard deviation images increases by that amount. However, it is not always necessary to calculate the respiratory feature amount from all the divided standard deviation images, but the respiratory feature amount may be calculated from at least a divided standard deviation image for a region that falls under a category of the chest region and a divided standard deviation image for a region that falls under a category of the abdominal region. For example, in a case where the division position data include a region division position between the abdominal region and the waist region and a region division position between the chest region and the shoulder region, one or both of the divided standard deviation image of the waist region and the divided standard deviation image of the shoulder region may not be used for calculating the respiratory feature amount.

Various examples of the respiratory feature amount will now be explained, but the respiratory feature amount may include one or a plurality of the examples to be described below, and are not limited to the examples to be described below. Of course, by calculating more types of respiratory feature amounts, the respiratory function of the subject 90 can be more comprehensively grasped.

Example of Respiratory Feature Amount: Average Value of Standard Deviation

For example, the feature amount calculation unit 16 can calculate the average value of the standard deviations indicated by the divided standard deviation image for each divided region as one of the respiratory feature amounts. The standard deviation for a certain pixel can be expressed as the standard deviation indicated by the pixel of the standard deviation image or can be expressed as the standard deviation indicated by the pixel of the divided standard deviation image.

With such a configuration, since the average value of the standard deviations is acquired for each divided region, it is possible to calculate the respiratory feature amount expressing a difference in the standard deviation between the divided regions in the standard deviation image. For example, an average value of standard deviations of the chest region and an average value of standard deviations of the abdominal region can be set as the respiratory characteristic amount. Alternatively, an average value of standard deviations of a left chest region, an average value of standard deviations of a right chest region, an average value of standard deviations of a left abdomen, and an average value of standard deviations of a right abdomen can be set as the respiratory feature amount. In either case, the average value calculated in this configuration example can be an index indicating, for example, a balance between expansion and contraction of a flank portion, which is an end region extending from the chest portion to the abdomen portion, i.e., a balance of expansion movement of the flank portion. Thus, the calculated average value can be used as a beneficial respiratory feature amount for evaluating a breathing motor function.

In particular, the feature amount calculation unit 16 may perform threshold processing for extracting a region having a standard deviation of a predetermined value or more with respect to the standard deviation image, and calculate a respiratory feature amount, based on the extracted standard deviation image. In short, the calculation of the respiratory feature amount may include extracting a region having a standard deviation of a predetermined value or more with respect to the standard deviation image, and calculating the respiratory feature amount, based on the extracted standard deviation image. Note that the method of calculating the respiratory feature amount including the threshold processing is not limited to the calculation of the average value of the standard deviations described above, and can also be applied to an example to be described later.

When the threshold processing is applied when the average value of the standard deviations is calculated, the feature amount calculation unit 16 first extracts a pixel having a standard deviation of a predetermined value or more in the standard deviation image. Next, the feature amount calculation unit 16 calculates an average value acquired by averaging standard deviations of the extracted pixel groups for each divided region, and sets the average value for each divided region as one of the respiratory feature amounts. By applying the threshold processing described above, for example, the pixel to be calculated includes a flank region having a large motion, and therefore, the calculated average value can be used as an index that indicates, in particular, the balance between expansion and contraction of the flank portion, i.e., the balance of expansion movement of the flank portion.

An example in which the threshold processing is applied to a case other than the case where the average value of the standard deviations is calculated will be described. The feature amount calculation unit 16 first executes extraction processing of extracting a pixel having a standard deviation of a predetermined value or more in the standard deviation image. Next, the feature amount calculation unit 16 can calculate an area of the extracted pixel group for each divided region, and can set the calculated area for each divided region as one of the respiratory feature amounts. The reason the area is referred to as herein is because the pixel has a size, and it can be expressed as an area even when only one pixel represents a standard deviation of a predetermined value or more. Therefore, the area of the extracted pixel group can mean the number of pixels of the pixel group. Hereinafter, the same applies to the area.

Example of Respiratory Feature Amount: Synchrony Between Divided Standard Deviation Images Further, the feature amount calculation unit 16 can also calculate a synchrony of the divided standard deviation images between the divided regions as one of the respiratory feature amounts. In other words, the feature amount calculation unit 16 can calculate a synchrony between the divided regions as one of the respiratory feature amounts, based on the divided standard deviation images.

Synchrony can be determined, for example, by similarity between each division standard deviation image, i.e., similarity in movement magnitude between segmented regions. A large standard deviation for a certain divided region means a large movement (movement from contraction to expansion) for that divided region. Therefore, the similarity between the divided standard deviation images can be regarded as one of indices of whether or not a certain divided region and another certain divided region are synchronized. When it is determined that a difference in movement between a certain divided region and another certain divided region, which is not less than a certain value, is not similar to each other, it can be considered that the divided regions are not synchronized with each other.

The similarity can be determined to be dissimilar, for example, when an average value for each divided standard deviation image is calculated and the average values are compared and separated by a predetermined value or more, or similar when the average values are separated by less than a predetermined value. For example, the following determination can be performed between the divided regions due to the left-right difference. Namely, first, one of the divided standard deviation images is inverted with respect to the left and right central axes, i.e., the intersection line between the sagittal plane and the frontal plane. Then, for the inverted divided standard deviation image and another divided standard deviation image, standard deviations at each pixel are compared one-to-one, and it is determined whether there is a separation of a predetermined value or more. As a result of the determination on all the pixels, when there is a separation equal to or larger than a predetermined value in a predetermined number of pixels or more, it is determined that the divided standard deviation images are dissimilar, and otherwise, it is determined that they are similar. Of course, the method of determining the similarity is not limited to these examples.

Further, the feature amount calculation unit 16 can also perform processing of specifying a region having a movement equal to or larger than a predetermined amount among the divided regions, based on the calculated synchrony. In short, the calculated synchrony can be used in order to determine a moving part, for example, to distinguish between movement of chest only, movement of abdomen only, both movements, and both no movement. Synchronization between a certain divided region and another certain region is indicative of either movement or no movement in both divided regions. Further, by referring to the value of the divided standard deviation image for each divided region, it is also possible to specify which of them is pertinent to. On the other hand, the lack of synchronization indicates that only one divided region moves and there is no movement in another divided region, and it is also possible to specify which of the divided regions is pertinent to by referring to the value of the divided standard deviation image for each divided region.

In a case where the above-described threshold processing is applied when calculating the above-described synchrony, the feature amount calculation unit 16 can first execute the above-described extraction processing and calculate the synchrony between the divided regions for only the extracted pixel group. As a result, it is possible to calculate the synchrony between the divided regions, based on only the pixel group having a large movement between the divided regions. In addition, the synchrony calculated in this way can also be used in order to identify a region having a movement of a predetermined amount or more among the divided regions as described above.

As described above, the synchrony between the divided regions can be calculated by determining the similarity between the divided standard deviation images. However, in the similarity between the divided standard deviation images, it is possible to grasp the synchrony of the magnitude of movement between the divided regions and the synchrony over the entire acquisition period of the time-series distance image data, but it is not possible to grasp the synchrony in consideration of a phase difference between the divided regions.

In order to grasp the phase difference, the feature amount calculation unit 16 can also calculate the synchrony between the divided regions from the acquired image data such as time-series distance image data. In other words, the synchrony of each divided region can be calculated, for example, based on time-series region-specific distance image data acquired by dividing the acquired time-series distance image data by the divided region. Note that, although the description is omitted, the same calculation can be performed from time-series image data that captures a movement other than the time-series distance image data.

As an example, a simplified example in which the divided region is a chest region and an abdominal region is exemplified, but the present disclosure is not limited thereto. In this case, the time-series distance image data can be divided into chest waveform data, which is data of the chest region, and abdominal waveform data, which is data of the abdominal region, as the time-series region-specific distance image data. The feature amount calculation unit 16 can calculate the synchrony between the divided regions as the respiratory feature amount, based on the waveform data.

The time-series distance image data include expiratory phase data, which are data associated to an expiratory phase of the subject 90, and inspiratory phase data, which are data associated to an inspiratory phase. In this example, the expiratory phase data are expiratory phase data for each of the chest waveform data indicating a breathing waveform of the chest portion of the subject 90 and the abdominal waveform data indicating a breathing waveform of the abdomen portion of the subject 90. The inspiratory phase data are inspiratory phase data for each of the chest waveform data and the abdominal waveform data. Of course, the expiratory phase data and the inspiratory phase data may be, for example, a series of data as the data, and in this case, any data that can be distinguished between the expiratory phase and the inspiratory phase may be used. For example, information capable of distinguishing between the expiratory phase and the inspiratory phase may be added in the chest waveform data, and information capable of distinguishing between the expiratory phase and the inspiratory phase may be added in the abdominal waveform data.

Division of the expiratory phase data and the inspiratory phase data can also be performed as follows. Namely, the feature amount calculation unit 16 calculates average waveform data of the abdominal waveform data and the chest waveform data, and divides each of the abdominal waveform data and the chest waveform data into the expiratory phase data and the inspiratory phase data, based on the average waveform data.

Herein, the reason why the average waveform data are used will be described supplementarily. When the breathing is such that the phases of the chest portion and the abdomen portion are shifted, peaks of the chest waveform data and the abdominal waveform data are shifted from each other. Therefore, when the expiratory phase and the inspiratory phase are calculated based on the peak and the like independently of the chest waveform data and the abdominal waveform data, the ratios of the expiratory phase and the inspiratory phase differ between the chest portion and the abdomen portion. In order to calculate the phase difference by comparing the associated phases of the chest waveform data and the abdominal waveform data, the above-described ratios need to be the same. Therefore, the division position between the expiratory phase and the inspiratory phase (a position at which the phase changes during one breathing cycle) is determined by using the average waveform data.

Regardless of the method of dividing the time-series distance image data into the expiratory phase data and the inspiratory phase data, for example, a change in a certain region of the chest region can be detected in the time-series distance image data, or the change can be detected by using a $CO_2$ sensor or the like. Note that the $CO_2$ sensor is a sensor that detects a ratio of carbon dioxide to a nose or the like of the subject 90, and can be used for breath analyses. Alternatively, for example, the average waveform may be displayed on the display device 30 or the like, and a division instruction operation by the instructor may be accepted and division may be performed according to the operation. Alternatively, the feature amount calculation unit 16 may analyze the average waveform data, detect the peak, and divide the expiratory phase and the inspiratory phase according to a predetermined rule, based on the detected peak. Alternatively, the feature amount calculation unit 16 may be configured to divide the expiratory phase and the inspiratory phase by using a machine learning technique such as a hidden Markov model.

The feature amount calculation unit 16 can calculate the synchrony between the chest region and the abdominal region by calculating the phase difference between the chest waveform data and the abdominal waveform data in each of the divided expiratory and inspiratory phases. The feature amount calculation unit 16 may calculate at least one phase difference for the expiratory phase and calculate at least one phase difference for the inspiratory phase. The calculation of the phase difference can be performed, for example, by comparing the peaks of the chest waveform data and the abdominal waveform data. In an example in which the expiratory phase and the inspiratory phase are divided from the average waveform, the phase difference calculated here can be said to be an estimated value.

The method of calculating the phase difference in each phase by the feature amount calculation unit 16 is not limited. For example, the feature amount calculation unit 16 may perform Hilbert conversion on the abdominal waveform data and the chest waveform data in the expiratory phase and calculate a successive phase (an instantaneous phase) for each of the abdomen portion and the chest portion. Similarly, the feature amount calculation unit 16 may perform Hilbert conversion on the abdominal waveform data and the chest waveform data in the inspiratory phase and calculate a successive phase (an instantaneous phase) for each of the abdomen and the chest. Then, the feature amount calculation unit 16 calculates a phase difference between the instantaneous phase of the abdomen portion and the instantaneous phase of the chest portion, which are calculated in this manner.

Further, in order to reduce the number of data, the feature amount calculation unit 16 can normalize the calculated phase difference in such a way that a length of the series expresses one breathing cycle at 100%, for example, take an average in units of 10%, and calculate 10 average phase differences. By such normalization, the breathing waveform can be divided for each breath, and a length of each breath can be unified. Of course, a period of the target to be averaged at this time is not limited to 10%, and the average phase difference of the number in response to the period is calculated. In addition, in a simple example, only two values of the average phase difference in the expiratory phase and the average phase difference in the inspiratory phase may be calculated for one breathing cycle. In addition, other statistical values such as a median value may be calculated instead of the calculation of the average value. As described above, the feature amount calculation unit 16 may calculate the phase difference during the normalized breathing cycle for the inspiratory phase data and the expiratory phase data.

In this way, the phase difference between the abdominal waveform data and the chest waveform data in the expiratory phase of the subject 90 is calculated, and the phase difference between the abdominal waveform data and the chest waveform data in the inspiratory phase of the subject 90 is calculated, and therefore, the phase difference in each phase can be acquired.

Based on the calculated phase difference, the feature amount calculation unit 16 can acquire, as one of the respiratory feature amounts, information indicating synchronization, such as which of the expiratory phase and the inspiratory phase is out of synchronization or which phase is more likely to be out of synchronization.

As described above, the synchrony of each divided region is not limited to being calculated based on the divided standard deviation image, and may be calculated from image data such as acquired time-series distance image data in addition to or instead of the calculation method.

Example of Respiratory Feature Amount: Expanded Area of Flank Region

The feature amount calculation unit 16 can also calculate an expansion area that is a difference in area from an expansion state to a contraction state of a flank region. The expansion area of this flank region is a value that can represent a movement of the flank region in a direction perpendicular to at least a sagittal plane and can therefore be used as one of the respiratory feature amount. Also in this example, the expansion area of the flank region as one of the respiratory feature amounts can be calculated based on the divided standard deviation image.

Herein, the flank region is a region which can expand and contract in a direction of an intersection line between a frontal plane and a transverse plane of the subject 90 (i.e., a direction perpendicular to the sagittal plane) in both the chest region and the abdominal region. Also, an expansion state may refer to a direction perpendicular to the sagittal plane, for example, the most expanded state. The contraction state may refer to a direction perpendicular to the sagittal plane, for example, the most contracted state, although errors may also be taken into account. For example, each of the expansion state and the contraction state may refer to a second expanded state, a second contracted state, or the like. Further, since the expansion area is an area in which a flank portion is expanded from the contraction state to the expansion state, it can also be referred to as an expansion area. Although explanation is made by defining the flank region as a region associated to the expansion area, the flank region itself can be specified by another definition, and in this case, the area of the region in which contraction and expansion are repeated in the flank region can be defined as the expansion area.

It can be said that the flank region exists over the chest region and the abdominal region, and does not exist in the shoulder region or the waist region. Therefore, the feature amount calculation unit 16 can calculate the expansion area of the flank region by specifying the flank region, based on the divided standard deviation image of the chest region and the divided standard deviation image of the flank region and calculating the expansion area of the flank region.

For example, the feature amount calculation unit 16 can extract a region of a pixel group having a standard deviation equal to or greater than a predetermined value, based on the divided standard deviation image of the chest region and the divided standard deviation image of the abdominal region, and by using the extracted region as a flank region, calculate an expansion area of the flank region. Of course, it is also possible to extract a region having a predetermined value or more in the standard deviation between the chest region and the abdominal region, to set an area equal to or larger than the predetermined area at a right end as a right-side expansion area, and to set an area equal to or larger than the predetermined area at a left end as a left-side expansion area, and to add them and form the expansion area.

This calculation method is equivalent to an example of a calculation method using the above-described threshold processing. However, the predetermined value is generally set to a value that exceeds a standard deviation due to a change in distance that may occur in the chest region or the abdominal region, and therefore, the expansion area of the flank region can be calculated.

The setting of the predetermined value is supplemented. In the flank region associated to the expansion area, i.e., the portion that expands and contracts in a direction perpendicular to the sagittal plane, a distance value changes from a distance where the body exists to a distance where the body does not exist (e.g., a distance to a bed). Thus, the change in direction perpendicular to the frontal plane in the flank region is greater than the change in direction perpendicular to the frontal plane in another thoracic region and another abdominal region, and the standard deviation in the flank region is also greater than the another thoracic region and the another abdominal region. Therefore, the predetermined value for calculating the expansion area of the flank region is generally set to a value that exceeds a standard deviation due to a change in distance that may occur in the chest region or the abdominal region.

Alternatively, the feature amount calculation unit 16 may first extract a pixel having a standard deviation of a predetermined value or more in the standard deviation image, and determine whether or not only the extracted pixel group is pertinent to one of the chest region and the abdominal region. Then, the feature amount calculation unit 16 may calculate the area of the pertinent pixel group as the expansion area of the flank region. In this case, among the extracted pixel groups, those pertinent to the chest region and the abdominal region become the pixel group associated to the expansion area of the flank region, and the pixel group pertinent to the shoulder region is not subject to the calculation of the expansion area. However, the predetermined value to be used in the extraction herein is also set as the value set as described above.

Further, the feature amount calculation unit 16 may calculate an expansion area for each of the right-side flank region and the left-side flank region, and may use these as the respiratory feature amount.

Example of Respiratory Feature Amount: Average Value of Standard Deviations of Flank Region The feature amount calculation unit 16 can also calculate the average value of the standard deviations indicated by the standard deviation image in the flank region as one of the respiratory feature amounts. The flank region can be detected as, for example, a region associated to the expansion area in the chest region and the abdominal region as described above. Further, the feature amount calculation unit 16 may calculate an average value of standard deviations indicated by the standard deviation image for each of the right-side flank region and the left-side flank region, and may use these values as respiratory feature amounts.

Example of Respiratory Feature Amount: Expansion Area of Shoulder Region

The feature amount calculation unit 16 can also calculate an expansion area, which is a difference in area of a shoulder expansion and contraction region in the shoulder region from the expansion state to the contraction state. The expansion area of the shoulder expansion and contraction region can be used as one of the respiratory feature amount because it is a value that can represent a movement in a direction perpendicular to at least the transverse plane (horizontal plane) in the shoulder region.

Herein, the shoulder expansion and contraction region is a region that can expand and contract in the direction of the intersection line between the frontal plane and the sagittal plane of the subject 90 in the shoulder region (i.e., a direction perpendicular to the transverse plane). Also, an expansion state may refer to a direction perpendicular to a transverse plane, for example, the most expanded state. The contraction state may refer to a direction perpendicular to the transverse plane, for example, the most contracted state, but the error may also be taken into account as described for the flank region. In addition, since the expansion area here is an area in which the shoulder portion is expanded from the contraction state to the expansion state, it can also be referred to as an expansion area.

It can be said that the shoulder expansion and contraction region exists in the shoulder region and does not exist in the chest region, the abdomen region, and the waist region. Therefore, the feature amount calculation unit 16 can specify the shoulder expansion and contraction region, based on the divided standard deviation image of the shoulder region, and calculate the area of the shoulder expansion and contraction region as the expansion area.

For example, the feature amount calculation unit 16 can extract a region of a pixel group having a standard deviation of a predetermined value or more, based on the divided standard deviation image of the shoulder region, and calculate an expansion area of the shoulder expansion and contraction region by using the extracted region as the shoulder expansion and contraction region. Of course, it is also possible to extract a region having a predetermined value or more in the standard deviation of the shoulder region, to set an area equal to or larger than the predetermined area of a right end as a right-side shoulder expansion area, and to set an area equal to or larger than the predetermined area of a left end as a left-side shoulder expansion area, and to add them and to form the expansion area.

This calculation method is also equivalent to an example of a calculation method using the above-described threshold processing, as explained above with respect to the calculation of the expansion area of the flank region. However, the predetermined value is set to a value that exceeds the standard deviation due to a change in the distance that can generally occur in the shoulder region, and therefore, the expansion area of the shoulder expansion and contraction region can be calculated.

The setting of the predetermined value is supplementarily described. In the shoulder expansion and contraction region associated to the expansion area that may occur in the shoulder portion, i.e., a portion that expands and contracts in a direction perpendicular to the transverse plane, the distance value changes from the distance where the body exists to the distance where the body does not exist (e.g., a distance to the bed). Therefore, a change in a direction perpendicular to a transverse plane in the shoulder region is greater than a change in the direction perpendicular to the transverse plane in another shoulder region, and the standard deviation in the shoulder expansion and contraction region is also greater than in the another shoulder region. Therefore, the predetermined value for calculating the expansion area of the shoulder expansion and contraction region is generally set to a value that exceeds a standard deviation due to a change in distance that may occur in the shoulder region.

Alternatively, the feature amount calculation unit 16 can first extract a pixel having a standard deviation of a predetermined value or more in the standard deviation image, determine whether or not only the extracted pixel group is pertinent to the shoulder region, and calculate the area of the pertinent pixel group as the expansion area of the shoulder expansion and contraction region. In this case, among the extracted pixel groups, those pertinent to the shoulder region become a pixel group associated to the expansion area of the shoulder expansion and contraction region, and the pixel groups pertinent to the chest region and the abdominal region are not subject to the calculation of the expansion area. However, the predetermined value to be used in the extraction here is also set as the value set as described above.

In addition, the feature amount calculation unit 16 may calculate an expansion area for each of the right-side shoulder expansion and contraction region and the left-side shoulder expansion and contraction region, and may use the calculated expansion area as the respiration feature amount.

Example of Respiratory Feature Amount: Average Value of Standard Deviation of Shoulder Region The feature amount calculation unit 16 can also calculate the average value of the standard deviations indicated by the standard deviation image in the shoulder expansion and contraction region as one of the respiratory feature amounts. The shoulder expansion and contraction region can be detected, for example, as a region associated to the expansion area in the shoulder region as described above. Further, the feature amount calculation unit 16 may calculate an average value of the standard deviations indicated by the standard deviation image for each of the right-side shoulder expansion and contraction region and the left-side shoulder expansion and contraction region, and may use these values as the respiratory feature amount.

Evaluation Unit 17

The evaluation unit 17 acquires an evaluation label by inputting a respiratory feature amount calculated by the feature amount calculation unit 16 to the learned model. The learned model is a learning model that is machine-learned in such a way as to input a respiratory feature amount and output an evaluation label that evaluates a respiratory function of a subject associated to the respiratory feature amount, and can be said to be an estimation model that estimates an evaluation label from the respiratory feature amount. This evaluation label included in a data set used during machine learning can be attached by an expert. This data set will contain data sets for many subjects 90 to be learned.

The respiratory feature amount calculated by the feature amount calculation unit 16 is based on at least a movement of the chest portion and a movement of the abdomen portion of the subject 90, and is a feature amount necessary for evaluating the breathing motor function. Then, the evaluation unit 17 estimates the evaluation label by using a result of machine learning the evaluation label as a result of the expert comprehensively performing the evaluation of the breathing motor function of the subject 90. Therefore, the evaluation unit 17 can estimate the evaluation result performed by the expert. In addition, by displaying the evaluation result on the display device 30 by the display control unit 19 to be described later, it is possible to understand the breathing movement, based on a result of the breathing movement evaluation performed by the expert, and to perform effective breathing training.

The evaluation label may include at least one of a subsequent first evaluation label and a subsequent second evaluation label.

The first evaluation label is a label that evaluates the respiratory function related to the movement of the subject 90 in a direction perpendicular to the frontal plane. The first evaluation label is an evaluation label associated to a respiratory feature amount related to a movement in a direction perpendicular to the frontal plane, such as an average value of the standard deviations. The expert will assign a first evaluation label, based on the respiratory feature amount related to the movement in a direction perpendicular to the frontal plane. In this case, the evaluation unit 17 can output the first evaluation label as the learned model using a first learned model in which the learning model is machine-learned by the data set including the respiratory feature amount and the first evaluation label.

The second evaluation label is a label that evaluates the respiratory function related to the movement of the subject 90 in a direction perpendicular to the sagittal plane. The second evaluation label is an evaluation label associated to a respiratory feature amount related to a movement in a direction perpendicular to the sagittal plane, such as a flank area or an expansion area of the shoulder expansion and contraction region. The expert will assign the second evaluation label, based on the respiratory feature amount related to the movement in the direction perpendicular to the sagittal plane. In this case, the evaluation unit 17 can output the second evaluation label as the learned model by using the first learned model in which the learning model is machine-learned by the data set including the respiratory feature amount and the second evaluation label.

When the evaluation label includes both the first evaluation label and the second evaluation label, the evaluation unit 17 may output the first evaluation label and the second evaluation label by using the first learned model and the second learned model as the learned model. As described above, the learned model to be used by the evaluation unit 17 may include the first learned model for outputting the evaluation label regarding the frontal perpendicular direction and include the second learned model for outputting the evaluation label regarding the sagittal perpendicular direction.

Alternatively, the evaluation unit 17 may output the first evaluation label and the second evaluation label by using a learned model in which the learning model is machine-learned by a data set including the respiratory feature amount, the first evaluation label, and the second evaluation label as the learned model. As described above, the learned model to be used by the evaluation unit 17 may be one learned model that outputs both the evaluation label regarding the frontal perpendicular direction and the evaluation label regarding the sagittal perpendicular direction.

Note that an existing machine learning model can be applied regardless of an algorithm or the like of the learned model to be used in the evaluation unit 17. As the machine learning model, for example, a classifying model such as a logistic regression model or Support Vector Machine can be applied. The learned model can be stored in the storage device or the storage unit 18 provided in the evaluation unit 17.

Storage Unit 18

The storage unit 18 is, for example, a storage device such as a memory or a hard disk. The storage unit 18 is, for example, a ROM (Read Only Memory), a RAM (Random Access Memory), or the like. The storage unit 18 has a function for storing a control program, an arithmetic program, and the like that are executed by the control unit 11. Further, the storage unit 18 has a function of temporarily storing data or the like during processing, and a function of storing target information for displaying data after processing on the display device 30 by the display control unit 19, which will be described later.

Display Control Unit 19

The display control unit 19 may include an interface such as a communication interface for wired or wireless connection to the display device 30. The display control unit 19 is an example of the output unit explained in the first example embodiment, and controls the display device 30 to display the calculated respiratory feature amount. Further, the display control unit 19 can also control the display device 30 to display the information indicating the standard deviation image and the division position or the division standard deviation image.

Further, the display control unit 19 may control the display device 30 to display the respiratory feature amount calculated by the feature amount calculation unit 16, or the respiratory feature amount and an advice to the subject 90 associated to the respiratory feature amount. In addition, the display control unit 19 may control the display device 30 to display the evaluation result acquired by the evaluation unit 17 or the evaluation result and an advice to the subject 90 associated to the evaluation result.

The display control unit 19 can also control the display device 30 to display a history of a display target, such as a history of the respiratory feature amount. Each piece of data serving as the history of the display target can be stored in the storage unit 18. The subject 90 can confirm a result of his/her breathing training and a change in the examination result by checking the history, and can make use of it in future.

In addition, the display control unit 19 may control the display device 30 to display a message to the subject 90 associated with the respiratory feature amount in advance, in addition to the advice to the subject 90. In addition, the display control unit 19 can also similarly control the display device 30 to display a message to the subject associated with the result in advance with respect to a result other than the respiratory feature amount, such as an evaluation result. Examples of the message other than the advice include a message indicating a feature such as a posture of the subject 90. Thus, in the present example embodiment, as an effect in a case where the result display is performed, the subject 90 or a therapist or the like of the subject 90 can determine a necessary training configuration, based on the result display.

Supplement for Each Component of the Information Processing Apparatus 10

Note that components of the image data acquisition unit 12, the standard deviation image calculation unit 13, the division position detection unit 14, the division unit 15, the feature amount calculation unit 16, the evaluation unit 17, and the display control unit 19 in the information processing apparatus 10 can be achieved by including, for example, a program. In short, each component can be achieved by executing a program under the control of the control unit 11, for example. More specifically, these components can be achieved by the control unit 11 executing a program stored in the storage unit 18. In addition, the necessary programs may be recorded in an optional nonvolatile recording medium and installed as necessary, and thereby achieve the components.

Further, each component is not limited to being achieved by software by a program, and may be achieved by any combination and the like of hardware, firmware, and software. In addition, each component may be achieved by use of an integrated circuit that is programmable by a user, such as a field-programmable gate array (FPGA) or a microcomputer. In this case, by use of the integrated circuit, a program composed of the above-described components may be achieved.

Processing Example of the Display System 100

Next, an example of processing in the display system 100 will be explained with reference to FIGS. 5 to 20. However, the processing in the display system 100 is not limited to the example explained below.

Figure 5:
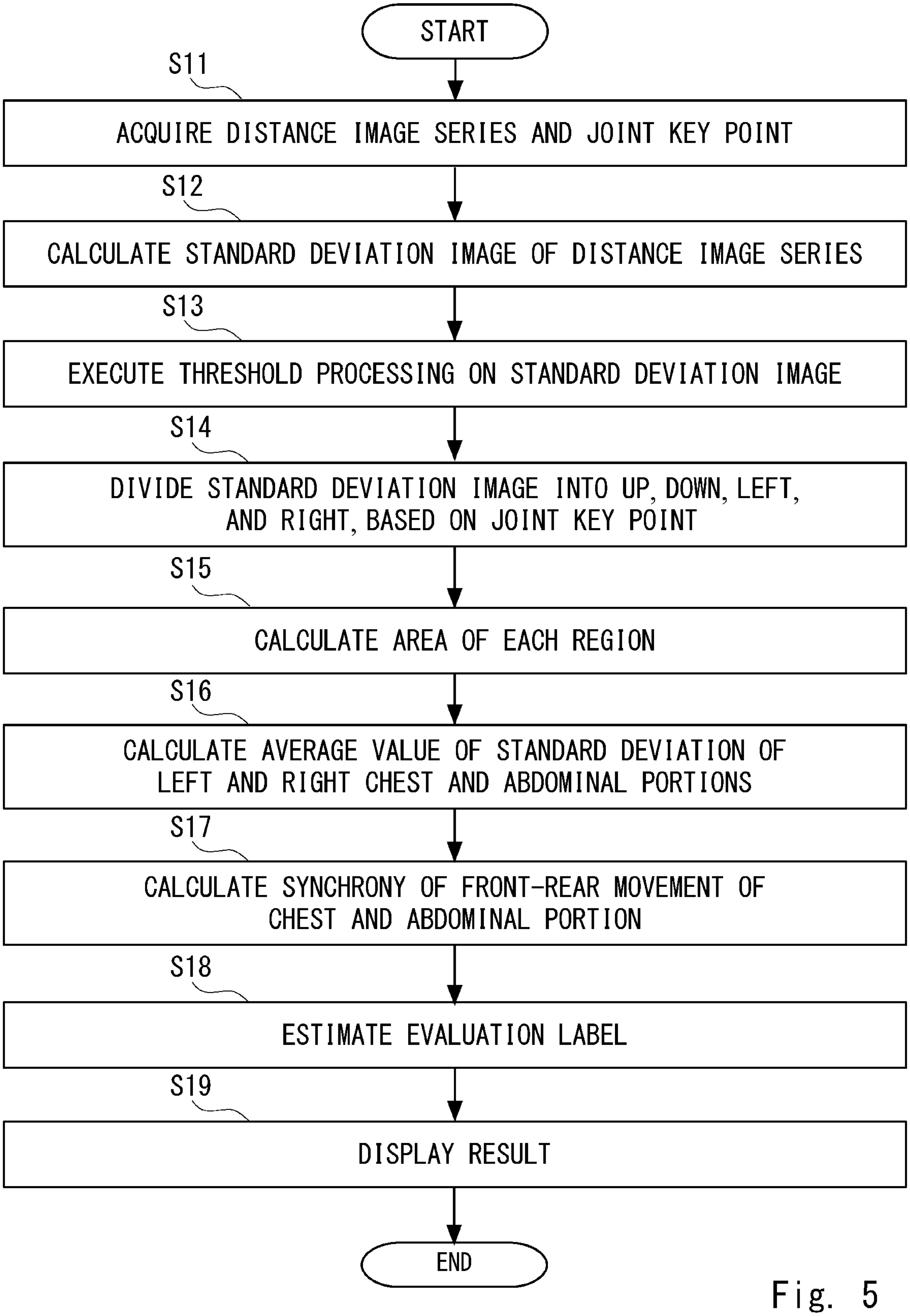
FIG. 5 is a flowchart for explaining an example of processing in the display system according to the present disclosure.
Figure 6:
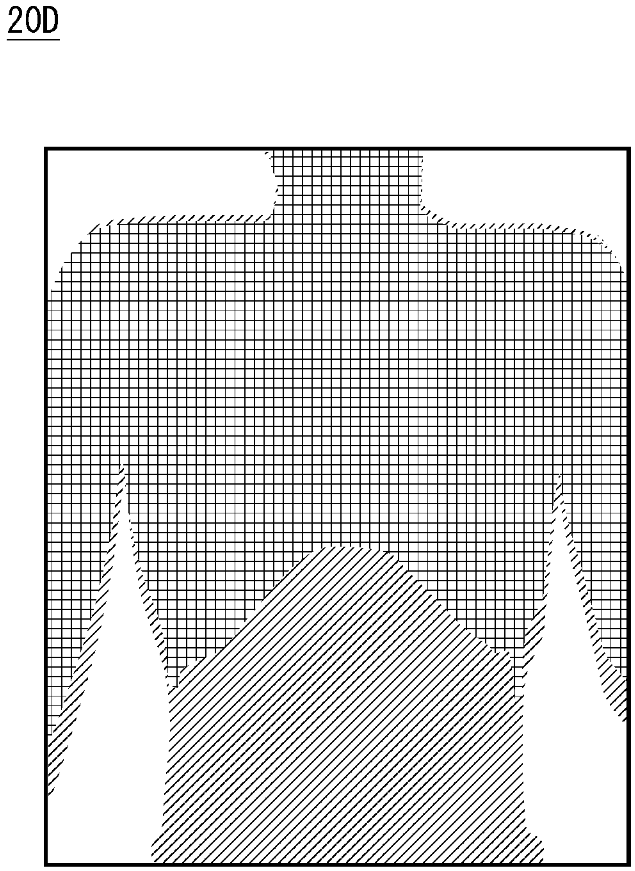
FIG. 6 is a schematic diagram illustrating an example of a distance image acquired by an imaging device in the display system according to the present disclosure.
Figure 7:
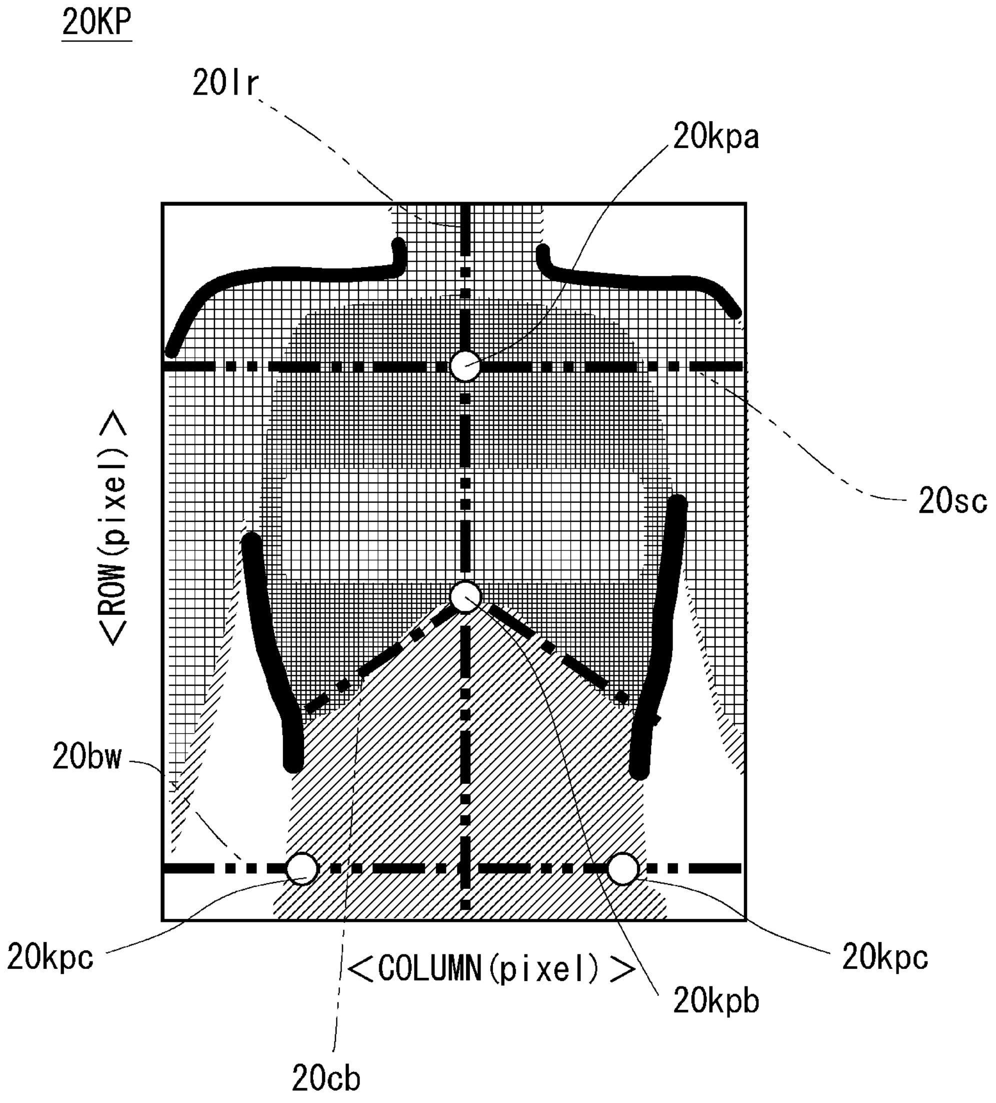
FIG. 7 is a schematic diagram illustrating an example of a standard deviation image calculated from the distance image by the information processing apparatus in the display system according to the present disclosure.
Figure 8:
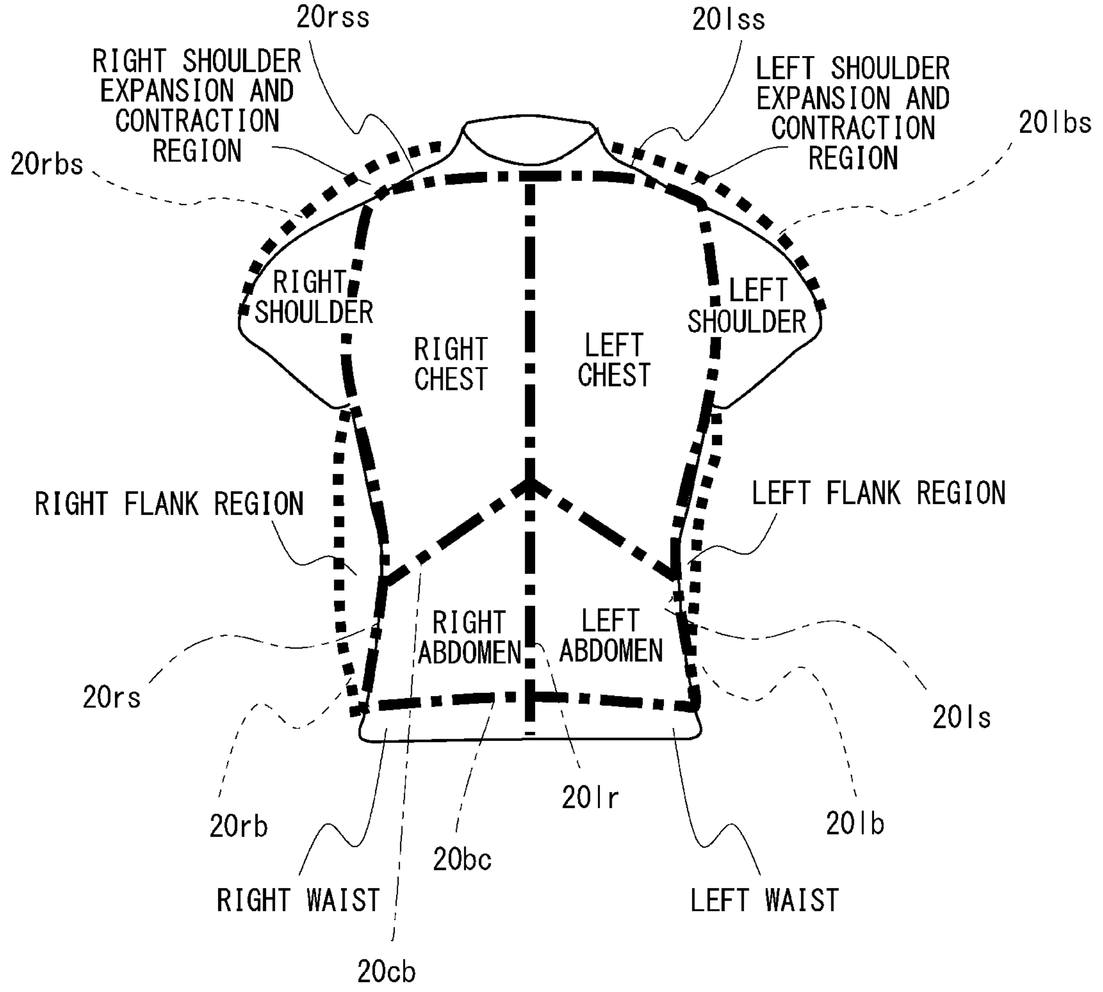
FIG. 8 is a schematic diagram illustrating an example of region division of a standard deviation image calculated by the information processing apparatus in the display system according to the present disclosure.

FIG. 5 is a flowchart for explaining an example of processing in the display system 100 according to the present disclosure. FIG. 6 is a schematic diagram illustrating an example of a distance image acquired by the imaging device 20 in the display system 100 according to the present disclosure. FIG. 7 is a schematic diagram illustrating an example of a standard deviation image calculated from the distance image in FIG. 6 by the information processing apparatus 10 according to the present disclosure. FIG. 8 is a schematic diagram illustrating an example of region division of a standard deviation image calculated by the information processing apparatus 10 according to the present disclosure, and is a schematic diagram illustrating an example of a divided region for calculating a respiratory feature amount.

First, in the information processing apparatus 10, the image data acquisition unit 12 acquires, from the imaging device 20, a distance image series acquired by measuring a distance from the subject 90 during a breathing exercise and a joint key point indicating a position of a joint of the subject 90 (step S11). The joint key point acquired in step S11 is part of the joint position data, and can be used in order to remove data of an unnecessary region from the distance image series, and can be used in division processing for dividing the standard deviation image.

The distance image at one time indicated by the distance image series can be, for example, a distance image 20D as illustrated in FIG. 6. In FIG. 6, for the sake of convenience, a difference in distance is represented by a difference in hatching, and only two distance values are represented in addition to the background. However, in practice, the distance value can, of course, include more values than the background distance. Further, in the following, an example in which the distance image 20D in FIG. 6 is a processing target will be described, but in the drawings illustrating the images of FIG. 6 and thereafter, for convenience, only an example of a processing result other than a shape of the body of the subject 90 is schematically illustrated.

Next, the standard deviation image calculation unit 13 performs preprocessing on the distance image data with respect to the distance image series, based on the joint key point, calculates a standard deviation for the distance image data after the preprocessing, and generates a standard deviation image (step S12). The pre-processing here may include, for example, processing of adjusting an orientation of the image and the like.

By the processing of step S12, a standard deviation image such as a standard deviation image 20KP illustrated in FIG. 7 is generated as the distance image 20D. In FIG. 7, the vertical axis represents a row of pixels (in units of pixels) and the horizontal axis represents a column of pixels (in units of pixels). The standard deviation image 20KP in FIG. 7 illustrates joint key points 20*kpa*, 20*kpb*, and 20*kpc* and dividing lines 20*sc*, 20*lr*, 20*cb*, and 20*bw* based on the joint key points in the generated standard deviation image. Hereinafter, for convenience, the standard deviation image generated in step S12 excluding the joint key points and the division lines in the standard deviation image 20KP in FIG. 7 will also be explained as “standard deviation image 20KP”.

Following step S12, the standard deviation image calculation unit 13 performs threshold processing on the standard deviation image 20KP (step S13). This threshold processing is processing for determining whether or not each standard deviation value, which is each pixel value of the standard deviation image 20KP, is equal to or greater than a predetermined value, and extracting a pixel group having a standard deviation value that is equal to or greater than the predetermined value.

Following step S13, the division position detection unit 14 detects a division position, based on the joint key points, and the division unit 15 divides the standard deviation image 20KP at the division position (step S14). In step S14, the standard deviation image 20KP can be divided into up and down by the dividing line 20*sc* and into left and right by the dividing line 20*lr*, based on the joint key point 20*kpa* at an upper end of the sternum, for example. The dividing line 20*lr* and the dividing line 20*sc* can be determined from a direction on the image by using only the joint key point 20*kpa*, but can also be determined by using the joint key point 20*kpb* at a pit of a stomach (a lower end of the sternum). Further, the dividing line 20*sc* may be determined based on a joint key point of a clavicle that is not illustrated.

Further, in step S14, the standard deviation image 20KP can be divided into a chest region and an abdominal region by the dividing line 20*cb*, based on the joint key point 20*kpb* of the pit of the stomach. The dividing line 20*cb* may be determined at a predetermined angle to the left and right with respect to the dividing line 20*lr*, for example. This predetermined angle can be set, for example, based on the average angle of the human ribs. Further, as will be described later with reference to FIG. 16 and the like, in order to more accurately determine the dividing line 20*cb*, the value of the standard deviation indicated by the standard deviation image 20KP can be used.

Further, in step S14, the standard deviation image 20KP can be divided into an abdominal region and a waist region by the dividing line 20*bw*, based on the joint key point 20*kpc* of an upper part of the pelvis (upper part of the ilium). Herein, the explanation of the division of the arm region is omitted. Further, in step S14, it is also possible to perform division processing on the image after the threshold processing in step S13.

By the division processing in step S14, for example, as indicated by a dashed-dotted line in FIG. 8, a portion of the upper body of the subject 90 excluding the head is divided. FIG. 8 illustrates an example in which as a result of the division processing, the standard deviation image is divided into a right chest, a left chest, a right abdomen, a left abdomen, a right shoulder, a left shoulder, a right waist, and a left waist.

Following step S14, the feature amount calculation unit 16 calculates the area of each divided region (step S15). In step S15, the feature amount calculation unit 16 calculates an area $S_{i,j}$ for each divided region for the pixel group having the predetermined value or more that has undergone the threshold processing in step S13.

$S_{i,j}$, where i∈{right, left}, j∈{shoulder, abdomen}

Note that the divided region for the area calculation target may include a right shoulder region, a left shoulder region, a right abdominal region, and a left abdominal region as in the above expression, and other regions may be excluded. However, since a part of the chest region may also be a flank region, areas of the right chest region and the left chest region may also be calculated.

In step S15, a magnitude of the expansion movement can be calculated by calculating the area for each divided region for the pixel group having a predetermined value or more that has undergone the threshold processing in step S13. Specifically, by the processing of step S15, the area indicating a magnitude of the expansion movement of the flank region in the flank portion is calculated as the number of pixels, and a magnitude of the expansion movement of the shoulder expansion and contraction region in the shoulder is calculated as the number of pixels. Therefore, the calculation result of step S15 can be used as a kind of the respiratory feature amount.

Supplementarily, the area of the expansion movement of the flank region can be expressed by the area of the right flank region and the area of the left flank region illustrated in FIG. 8. The right flank region is a region represented by a difference between a right flank outer edge 20*rs* at a time of contraction and a right flank outer edge 20*rb* at a time of expansion. The left flank region is a region represented by a difference between a left shoulder outer edge 20*lss* at the time of contraction and a left flank outer edge 20*lb* at the time of expansion. As illustrated in FIG. 8, the area of the expansion movement of the shoulder expansion and contraction region can be expressed by the area of the right shoulder expansion and contraction region and the area of the left shoulder expansion and contraction region. The right shoulder expansion and contraction region is a region expressed by a difference between a right shoulder outer edge 20*rss* at the time of contraction and a right shoulder outer edge 20*rbs* at the time of expansion. The left shoulder expansion and contraction region is a region expressed by a difference between a left shoulder outer edge 20*lss* at the time of contraction and a left shoulder outer edge 20*lbs* at the time of expansion.

Next to step S15, the feature amount calculation unit 16 calculates an average value $\mu_{i,k}^{SD}$ of the standard deviations of the divided standard deviation images for the left and right chest and abdomen portion, i.e., for the left and right chest regions and the left and right abdominal regions (step S16). As a result, it is possible to calculate the magnitude of the movement of the chest and abdomen portion in the front-rear direction (a direction perpendicular to the frontal plane). The unit of the magnitude may be, for example, mm.

$\mu_{i,k}^{SD}$, where i∈{right, left}, k∈{chest, abdomen}

Herein, the standard deviation to be used for the calculation in step S16 can be the standard deviation for the pixel group of each divided region that does not undergo the threshold processing described above, but the average value for each divided region can also be calculated for the pixel group that has undergone the threshold processing and is equal to or larger than a predetermined value. Regardless of the calculation target, the calculation result of step S16 can be used as a kind of the respiratory feature amount.

Next to step S16, the feature amount calculation unit 16 calculates a synchrony of the divided standard deviation image between the divided regions (step S17). The divided region to be calculated may be, for example, a chest region and an abdominal region, a left-side region and a right-side region, or a left-side chest region, a right-side chest region, a left-side abdominal region and a right-side abdominal region. As the method of calculating the synchrony, a method of calculating the similarity between the divided standard deviation images as described above or the like can be adopted. However, as described above, it is also possible to adopt a method of calculating the synchrony between divided regions from image data such as time-series distance image data. The order of steps S15 to S17 is not limited.

Next to steps S15 to S17, the evaluation unit 17 estimates the evaluation label by using the learned model (step S18). In step S18, the evaluation unit 17 inputs the respiratory feature amounts calculated in steps S15 to S17 to the learned model, and acquires an evaluation label as an output from the learned model, thereby estimating the evaluation label. Since there are a plurality of respiratory feature amounts to be input to the learned model, it can be said that a respiratory feature amount vector is input to the learned model.

Figure 9:
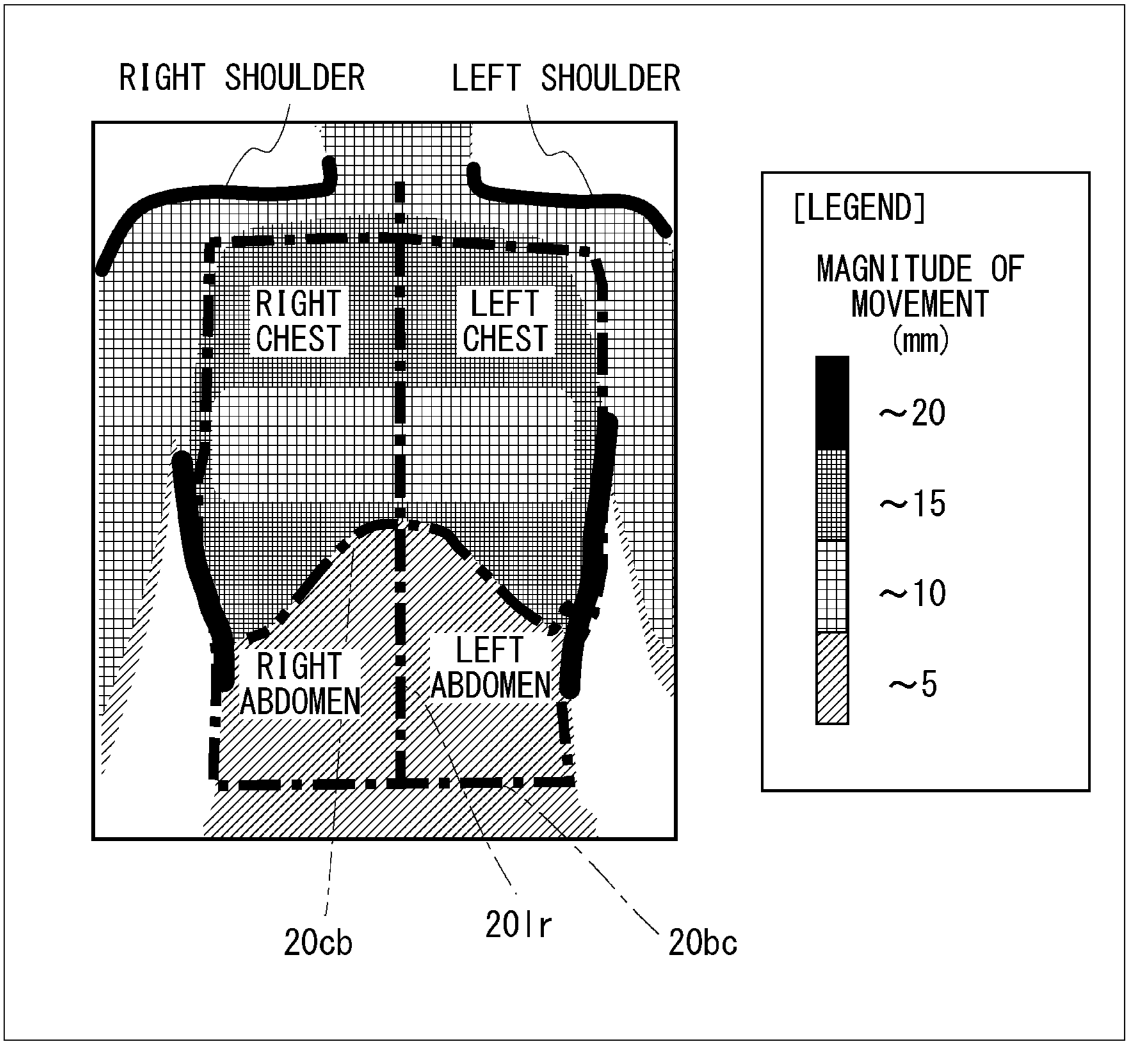
FIG. 9 is a diagram illustrating an example of a divided standard deviation image displayed on the display device under control of the information processing apparatus in the display system according to the present disclosure.

Prior to the description of step S18, an example of processing of generating a learned model, i.e., an example of processing in a learning step will be explained. First, an example of assignment of an evaluation label by an expert will be explained with reference to FIGS. 9 to 11. FIG. 9 is a diagram illustrating an example of a divided standard deviation image, which is displayed on the display device 30 under the control of the information processing device 10 according to the present disclosure. FIG. 10 is a diagram illustrating an example of an evaluation label according to the present disclosure, the evaluation label being acquired by evaluating a subject 90 as viewed from a side. FIG. 11 is a diagram illustrating an example of an evaluation label according to the present disclosure, the evaluation label being acquired by evaluating the subject 90 as viewed from a front.

By the processing of step S14, the chest and abdominal division processing and the left-right division processing for the standard deviation image 20KP are completed. Thereafter, the standard deviation image 20KP is displayed on the display device 30 together with the division result for reference when the expert attaches the evaluation label. Of course, it is assumed that the display device 30 serving as a display destination is a display device that can be viewed by an expert.

Such a display example will be explained. The display control unit 19 performs drawing such that the region division result indicated by the dividing lines 20*cb*, 20*lr*, and 20*bc* in FIG. 9 is superimposed on the standard deviation image 20KP, and causes the display device 30 to display the image of the drawing result, for example. In an image 30SL illustrated in FIG. 9, the dividing lines 20*cb* and 20*lr*, which are the results of the chest and abdominal division processing and the left-right division processing to be described later, are illustrated with reference to FIG. 16 and the like.

In the display control, as in the image 30SL illustrated in FIG. 9, an image including at least one of a legend indicating the magnitude of the motion indicated by the standard deviation value and the name of each divided region can be displayed. In the image 30SL, names "right chest", "left chest", "right abdomen", and "left abdomen" of the divided regions may be displayed on the outside of the standard deviation image by using a lead line or the like. Although FIG. 9 illustrates an example in which a difference between the standard deviation values is indicated by density of hatching, it can actually be expressed with a multi-color gradation. In the image 30SL, a result of dividing into the abdominal region and the waist region by the dividing line 20*bc* is also illustrated, and a result of dividing the chest region and the arm region is also illustrated, and these divisions can be executed based on joint key points.

Then, while confirming the image 30SL, the expert performs an input such as checking in blanks of an evaluation label 17*a* illustrated in FIG. 10 and an evaluation label 17*b* illustrated in FIG. 11. In the evaluation label 17*a*, the movement of the subject 90 as viewed from the side is evaluated as a moving part and presence or absence of a warp of the back, and the evaluation label 17*b* evaluates the movement of the subject 90 as a movement part and the presence or absence of the shoulder rise as viewed from the front. At this time, the expert may also input other evaluations of the breathing function of the subject 90.

The information of the evaluation being input by the expert is a part of a set of data (learning data set) for generating the learned model together with the calculated respiratory feature amount, and can be input to the non-learned model and machine learning can be performed. In addition, the training data set may include subject information such as gender, a breast size, and Body Mass Index (BMI) of the subject 90.

Next, a processing example of step S18 using the learned model thus generated, i.e., a processing example of an operation process will be explained. The evaluation unit 17 inputs respiratory feature amount vectors calculated in steps S15 to S17 to the learned model, and acquires output results of the evaluation label 17*a* in FIG. 10 and the evaluation label 17*b* in FIG. 11. However, the evaluation label 17*a* and the evaluation label 17*b* acquired in this case are filled with a blank as an output from the learned model. In addition, when other information such as subject information is included in the learning data set, this information can be input to the learned model in addition to the respiratory feature amount vector.

After step S18, the display control unit 19 causes the display device 30 to display an examination result of the subject 90 (step S19), and ends the processing. The examination result may include the evaluation labels 17*a* and 17*b*. The subject 90 or an instructor such as a therapist of the subject 90 can confirm the evaluation labels 17*a* and 17*b* and confirm the state of the breathing movement of the subject 90. When the display control unit 19 causes the evaluation labels 17*a* and 17*b* to be displayed on the display device 30, it is possible to understand the breathing movement based on the result of the breathing movement evaluation performed by the expert, and to perform effective breathing training. In addition, the display control unit 19 may cause the display device 30 to display an image indicating the movement of the subject 90 as in the image 30SL in FIG. 9.

Figure 12:
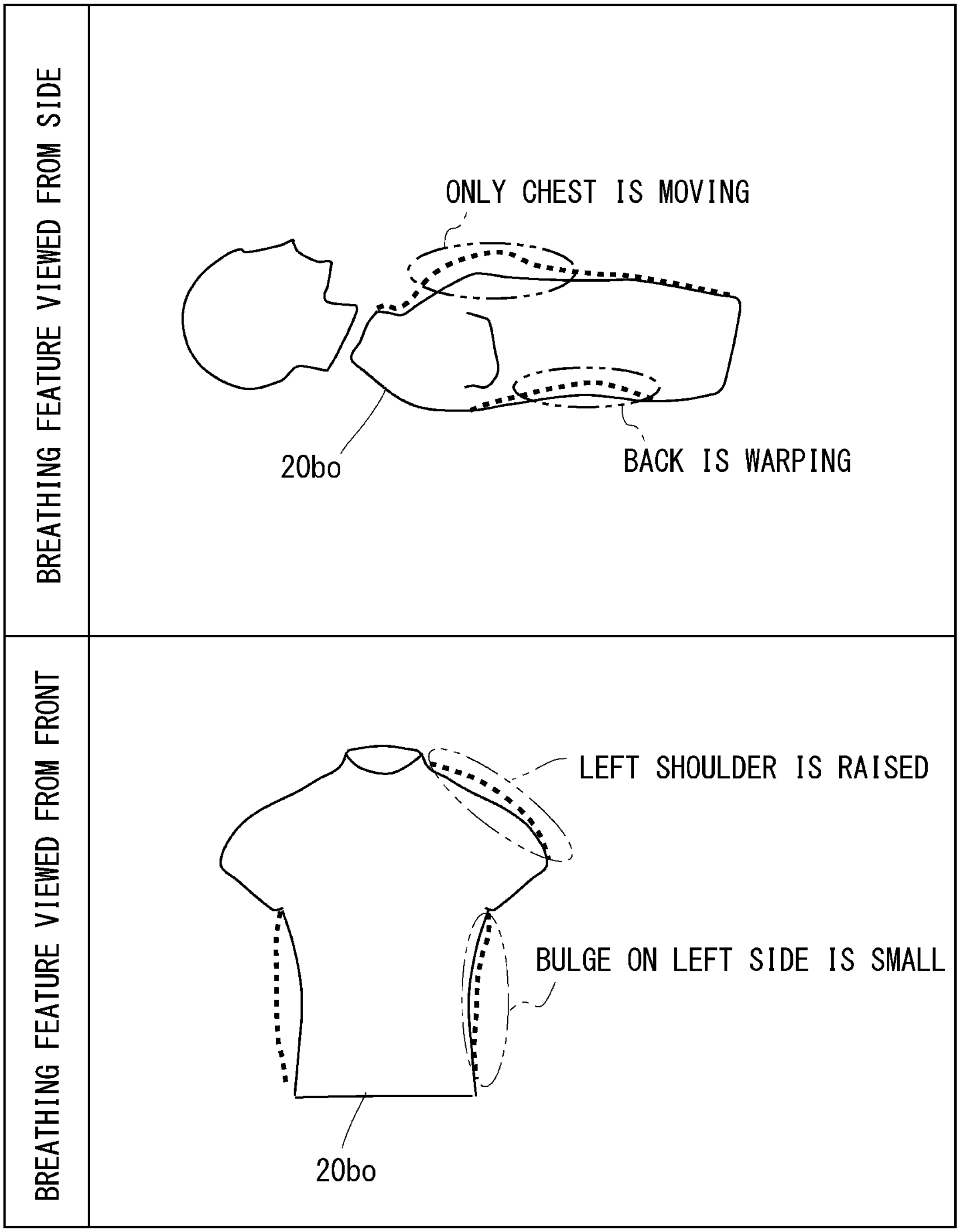
FIG. 12 is a diagram illustrating an example of a respiratory feature of a subject, which is displayed on the display device under control of the information processing apparatus in the display system according to the present disclosure.
Figure 13:
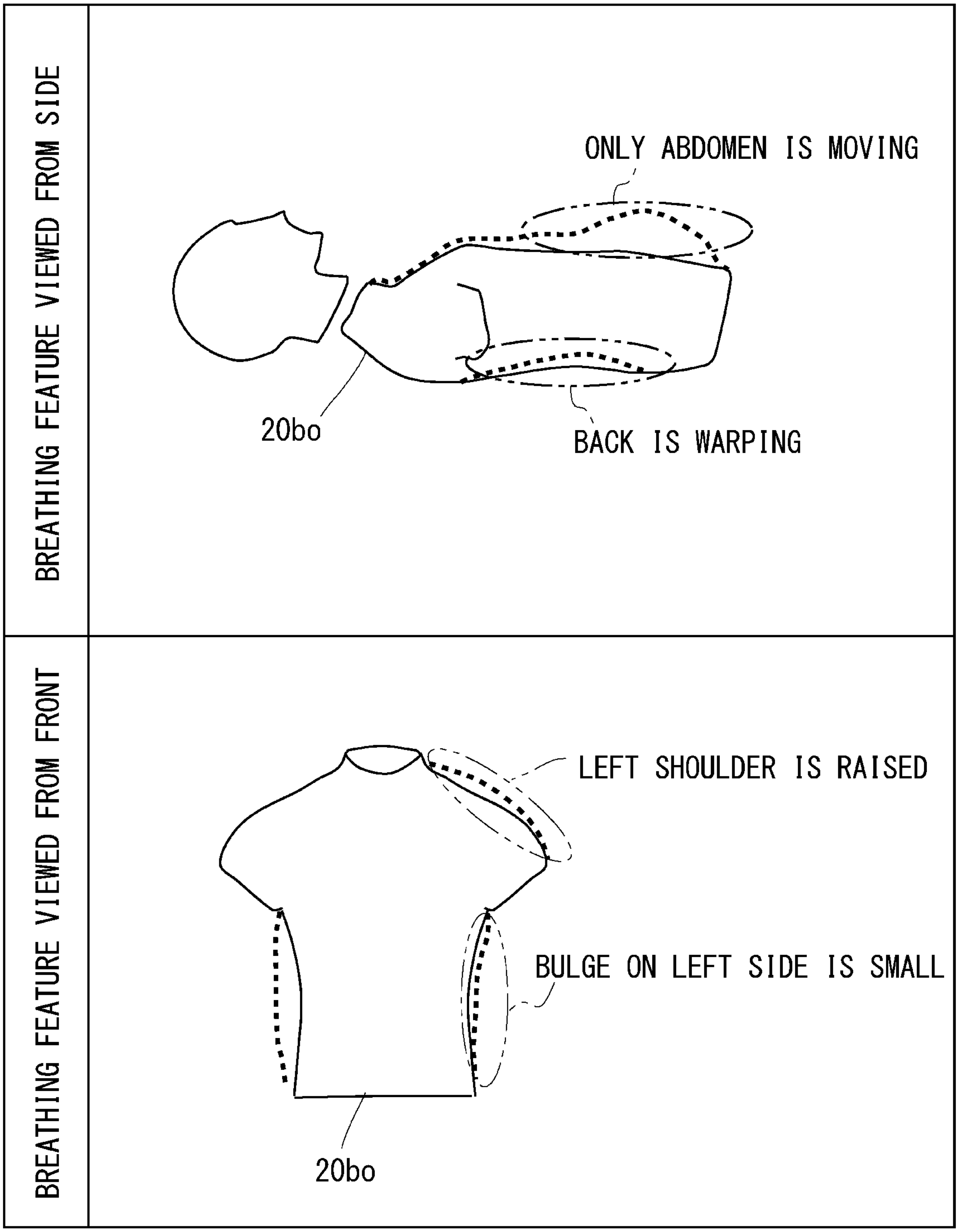
FIG. 13 is a diagram illustrating another example of the respiratory feature of the subject, which is displayed on the display device under control of the information processing apparatus in the display system according to the present disclosure.
Figure 14:
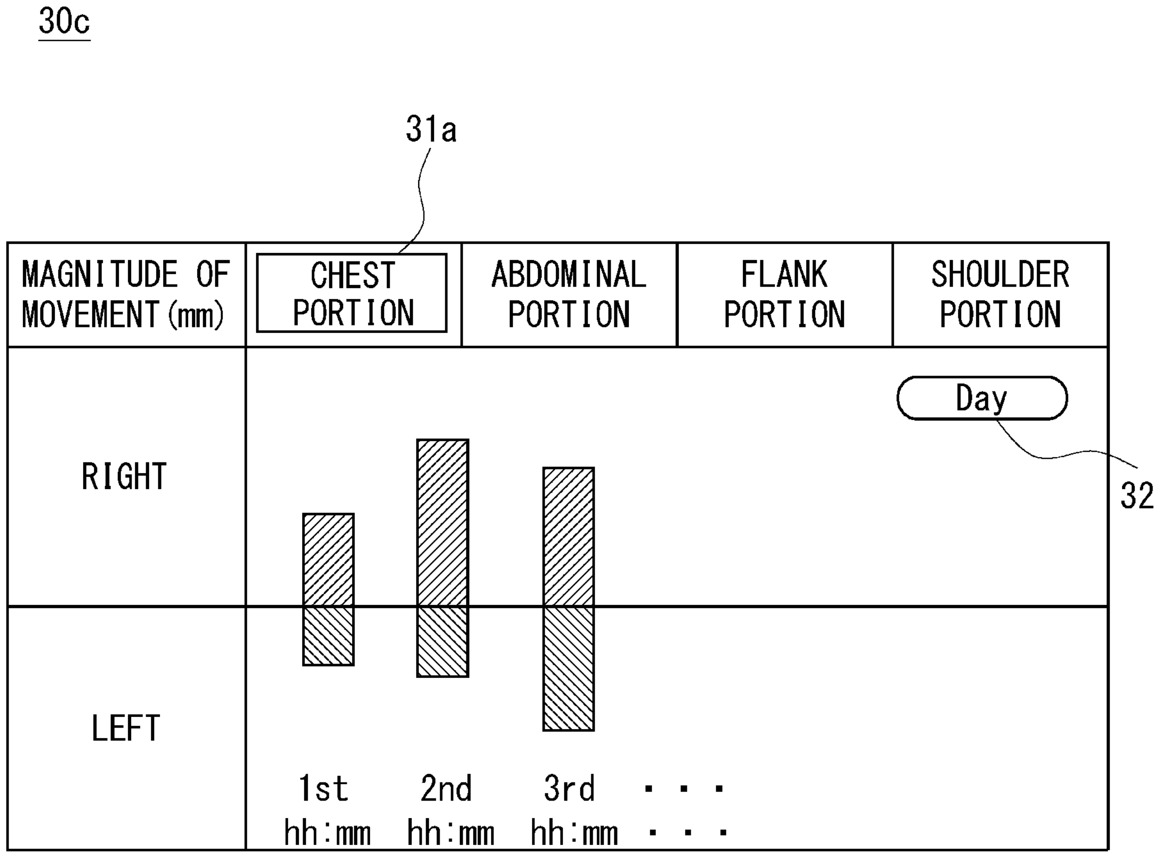
FIG. 14 is a diagram illustrating an example of the respiratory feature amount of the subject, which is displayed on the display device under control of the information processing apparatus in the display system according to the present disclosure.
Figure 15:
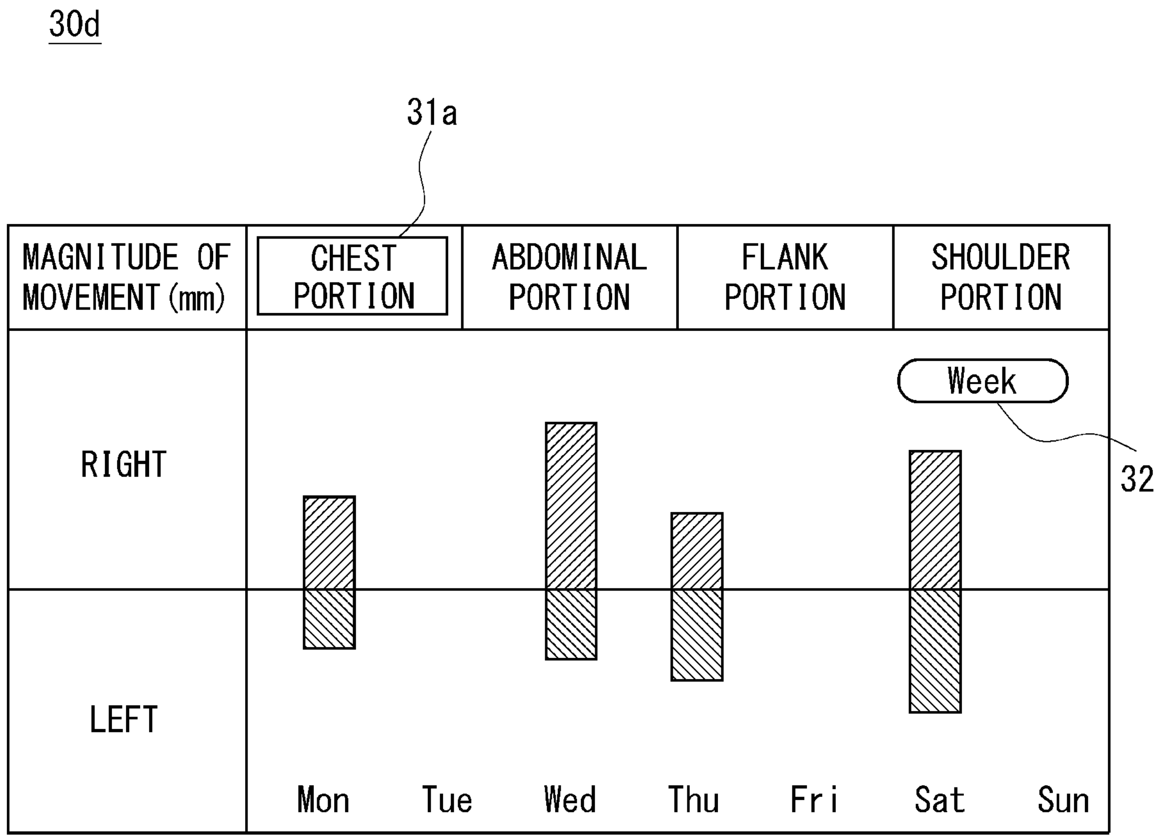
FIG. 15 is a diagram illustrating another example of the respiratory feature amount of the subject, which is displayed on the display device under control of the information processing apparatus in the display system according to the present disclosure.

Next, other display contents that can be displayed in step S19 will be explained with reference to FIGS. 12 to 15. FIG. 12 is a diagram illustrating an example of breathing features of the subject 90 displayed on the display device 30 under control of the information processing apparatus 10 according to the present disclosure. FIG. 13 is a diagram illustrating another example of breathing features of the subject 90 displayed on the display device 30 under control of the information processing apparatus 10 according to the present disclosure. FIG. 14 is a diagram illustrating an example of the respiratory feature amount of the subject 90 displayed on the display device 30 under control of the information processing apparatus 10 according to the present disclosure. FIG. 15 is a diagram illustrating another example of the respiratory feature amount of the subject 90 displayed on the display device 30 under control of the information processing apparatus 10 according to the present disclosure.

As illustrated in a display image 30*a* in FIG. 12, the display control unit 19 can also control the display device 30 to display a message, such as information indicating the posture of the subject 90, which is associated to the respiratory feature amount calculated by the feature amount calculation unit 16.

The display image 30*a* illustrated in FIG. 12 includes a state in which the features of the breathing of the subject 90 are viewed from the side and a state in which the features of the breathing of the subject 90 are viewed from the front. In addition, the display image 30*a* includes, in addition to an outline image 20*bo* indicating the subject 90, an outline line (indicated by a thick broken line) for expressing a magnitude of a movement for indicating the feature of the breathing, and a message indicating the feature of the breathing. Note that the display form of the outline line is not limited to this, and a color may be changed with respect to the outline image 20*bo*, or an outline image in a display form different from the outline image 20*bo* may be used instead of the outline line.

The display image 30*a* includes posture information indicating the posture of the subject during the breathing exercise as a message indicating the feature of the breathing. Herein, as the posture information, an example is given in which a message indicating that "only the chest is moving" and "the back is warping" is included in the breathing feature viewed from the side, and a message indicating that "the left shoulder is raised" and "a bulge on the left side is small" is included in the breathing feature viewed from the front. The subject 90 who has confirmed this message or is communicated from an instructor, such as a therapist, may perform breathing training to resolve the content of this message.

The display image 30*b* illustrated in FIG. 13 includes the same content as that of the display image 30*a,* but the calculated respiratory feature amount is different. Therefore, the display image 30*b* differs from the display image 30*a* in the shape of the outline line for expressing the magnitude of the movement for indicating the feature of the breathing, and also in part, in the posture information indicating the feature of the breathing. In the display image 30*b*, an example including the following message is given as the posture information. In other words, the message includes a message indicating that "only the abdomen is moving" and "the back is warped" in the breathing feature viewed from the side, and a message indicating that "the left shoulder is raised" and "a bulge on the left side is small" in the breathing feature viewed from the front.

Further, the message to be displayed may be stored in advance in association with the respiratory feature amount, and an associated message may be called in accordance with the respiratory feature amount. In addition, the message to be displayed may include advice to the subject 90 associated to the respiratory feature amount. Messages such as this advice may also include a message based on a history of respiratory feature amounts, i.e., based on a change in the respiratory feature amount that may be caused by breathing training or the like.

Alternatively, the message to be displayed may be stored in advance in association with the evaluation result, and an associated message may be called in accordance with the evaluation result. In short, the display control unit 19 can also control the display device 30 to display a message such as advice to the subject 90 associated to the evaluation result by the evaluation unit 17 and information indicating the posture of the subject 90. The message such as the advice may include a message based on the history of the evaluation result, i.e., based on a change in the evaluation result that may be caused by breathing training or the like.

Further, as illustrated in a display image 30*c* of FIG. 14, the display control unit 19 may control the display device 30 to display the respiratory feature amount calculated by the feature amount calculation unit 16. The display image 30*c* includes a history of respiratory feature amounts in each divided region, but may include only respiratory feature amounts calculated at the latest time.

Herein, in the display image 30*c,* values are included in the lower column and the upper column for left and right divided regions, and values of associated parts are displayed by selecting tabs for the chest portion, abdomen portion, flank portion, and shoulder portion. The display image 30*c* is a display content when a tab 31*a* of the chest portion is selected, and an average value of the standard deviations in the right-side chest region and an average value of the standard deviations in the left-side chest region according to the number of times of examination or breathing training are illustrated as a bar graph.

The subject 90 who has confirmed such a respiratory feature amount or has been communicated from an instructor such as a therapist can perform breathing training in such a way as to resolve the content. For example, referring to the first and second times, the subject 90 may perform breathing training in such a way as to average the right-side chest during a breathing exercise because the right-side chest moves more than the left-side chest during the breathing exercise.

Similarly, when a tab for the abdomen portion is selected, the average value of the standard deviations in the right flank region and the average value of the standard deviations in the left flank region according to the number of times of examination or breathing training can be displayed in a bar graph. When a tab for the flank portion is selected, the area of the right flank region and the area of the left flank region in response to the number of times of examination or breathing training can be displayed in a bar graph. If a shoulder tab is selected, the area of the right shoulder expansion and contraction region and the area of the left shoulder expansion and contraction region, as a function of the number of examinations or breathing training, may be displayed in a bar graph.

In the display image 30*c,* an example in which a history of the number of times of examination or breathing training in one day is displayed is illustrated. However, by selecting a button 32 for selecting a period of the history to be displayed, the daily history of the examination or the breathing training in one week from Monday to Sunday may be displayed, for example, as in a display image 30*d* illustrated in FIG. 15. As the daily history, for each day, for example, an average value in one day can be displayed. In the display image 30*d,* it can be seen that the button 32 is changed from the notation representing the day to a notation representing the week. Further, by selecting the button 32, the display period such as day, week, month, and year can be changed by a toggle method or a pull-down menu method.

Further, the display control unit 19 can also control the display device 30 to display the evaluation result by the evaluation unit 17. The evaluation result can be taken to be that which has been entered in, for example, each blank space of the evaluation labels 17*a* and 17*b*.

In the present example embodiment, as an effect when displaying a part or all of the various kinds of information as described above, the subject 90 or a therapist or the like of the subject 90 can determine a necessary training configuration, based on the display content thereof. The content to be displayed is not limited to the respiratory feature amount, the evaluation result, or a message associated therewith. The display control unit 19 may control the display device 30 to display various kinds of information such as other analysis results, or may control the display device 30 to display a message to a subject associated with the information in advance.

Effect of the Present Example Embodiment

Before explaining an example of the region division processing using the standard deviation image, effects of the present example embodiment will be explained. As can be seen from the above description, according to the present example embodiment, similarly to the first example embodiment, the respiratory feature amount indicating the feature of the breathing of the subject 90 can be calculated based on the movement of the chest and abdomen portion of the subject 90, and the respiratory feature amount necessary for the evaluation of the respiratory motor function of the subject 90 can be calculated.

Further, according to the present example embodiment, it is possible to evaluate the breathing motor function of the subject 90, based on the respiratory feature amount calculated in this manner as compared with the first example embodiment, and thus it is possible to improve the accuracy of the evaluation. This effect is supplementarily described. For example, an abnormal breathing pattern occurs in a musculoskeletal disorder such as a low back pain, and therefore, movement examination and movement evaluation of the chest and abdomen portion during a breathing exercise are important. In addition, since these examination and evaluation by experts are generic, objective and quantitative examination technique and evaluation technique are required. In the present example embodiment, the respiratory feature amount can be calculated based on the movement of each divided region, and even when the expert attaches the evaluation label in the learning stage, the respiratory feature amount can be attached with reference to the respiratory feature amount, so that it can be said that the accuracy of such examination and evaluation can be improved. In addition, in the present example embodiment, it is possible to improve the accuracy of the guidance using the evaluation, and thus it is possible to provide effective guidance.

Further, in the present example embodiment, for example, the average value of the standard deviations of the distance values of the left and right chest and abdominal regions, the expansion areas of the left and right shoulder portion and the flank portion, and the synchrony of the chest and abdominal portion in the front-rear direction can be calculated as the respiratory feature amount. These respiratory feature amounts are information that can cover the breathing motor function of the subject 90. Therefore, in the present example embodiment, it can be said that the accuracy of examination and evaluation can be further improved as compared with the first example embodiment.

Further, in the present example embodiment, the evaluation label of the motor function disorder or the like assigned by the expert can be estimated using a machine learning algorithm, and the calculated respiratory feature amount and the estimated evaluation label can be displayed. Therefore, in the present example embodiment, it can be said that the accuracy of the guidance using the respiratory feature amount and the evaluation can be improved as compared with the first example embodiment. Further, in the present example embodiment, by including the past history in the respiratory feature amount and the evaluation to be displayed, it is possible to confirm the result of the respiration training of the subject 90 and a change in the examination result and to make use of the result in the future. Accordingly, in the present example embodiment, it is possible to further improve the accuracy of the guidance using the respiratory feature amount and the evaluation.

In addition, in the present example embodiment, as in the first example embodiment, effective guidance can be performed by use of an instructor such as a therapist at a time of rehabilitation in a medical institution or breathing exercise practice in a healthcare service. Specifically, in the present example embodiment, as an effect of displaying a part or all of various pieces of information, the subject 90, a therapist of the subject 90, or the like can determine a necessary training configuration based on the display content. Further, in the present example embodiment, the information processing apparatus 10 or the information processing apparatus 10 and the display device 30 are mounted on a terminal device or the like to be used by a subject, whereby the subject can receive remote guidance from an instructor and perform voluntary training while being at home. In particular, by mounting the function of the information processing apparatus 10 as an application or the like in a portable terminal device such as a tablet terminal to be used by a subject, it becomes easier for the subject 90 to perform breathing training and examination. The imaging device 20 can also use a camera or the like mounted on the terminal device.

Region Division Processing Using Standard Deviation Image

Figure 16:
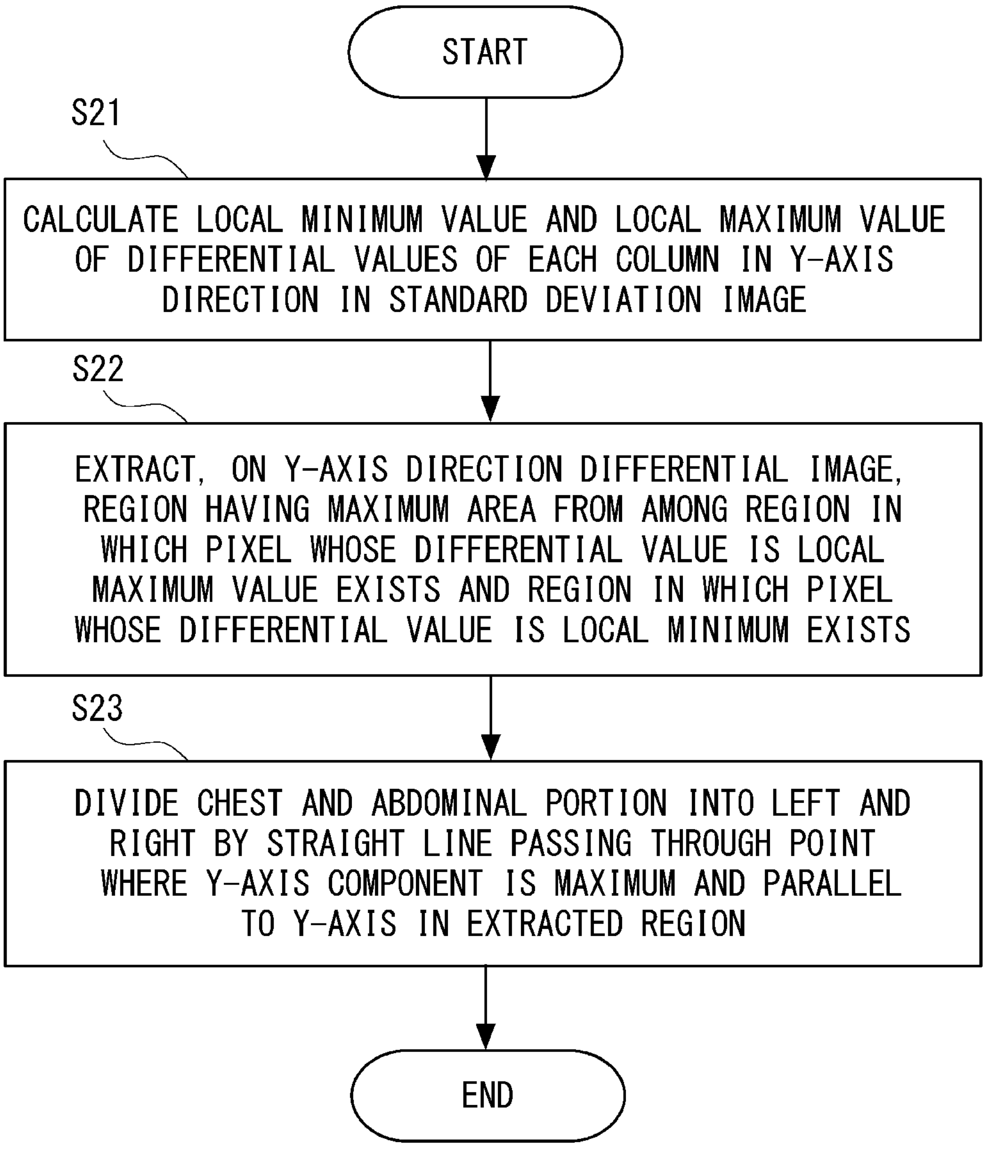
FIG. 16 is a flowchart for explaining an example of chest and abdominal division processing and left-right division processing in the display system according to the present disclosure.
Figure 17:
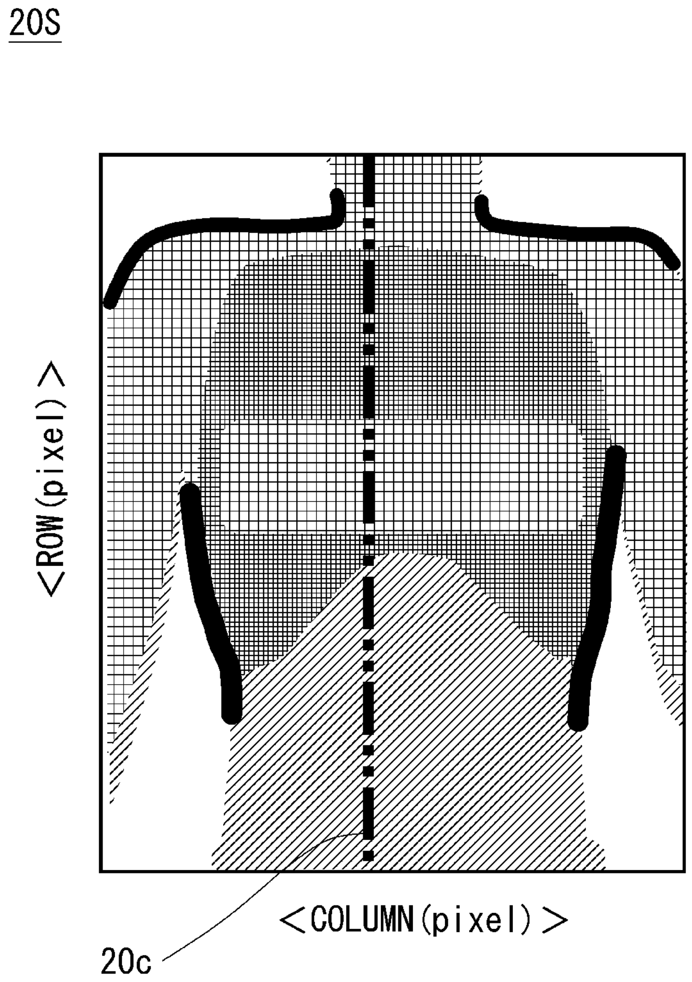
FIG. 17 is a schematic diagram illustrating an example of the standard deviation image calculated from the distance image by the information processing apparatus in the display system according to the present disclosure.
Figure 18:
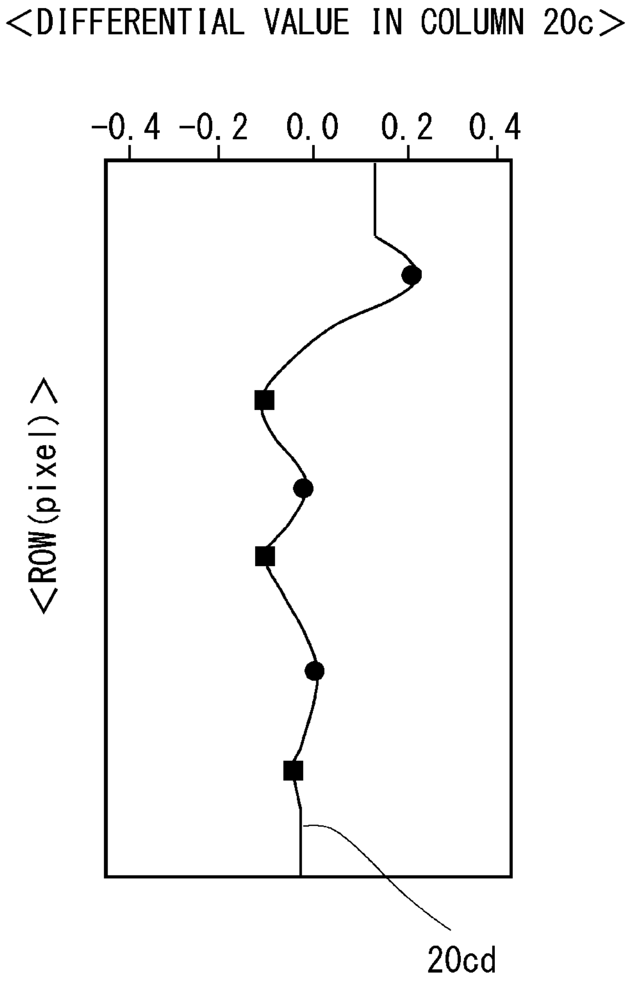
FIG. 18 is a graph illustrating an example of a differential value calculated for a certain pixel column in the standard deviation image by the information processing apparatus in the display system according to the present disclosure.
Figure 19:
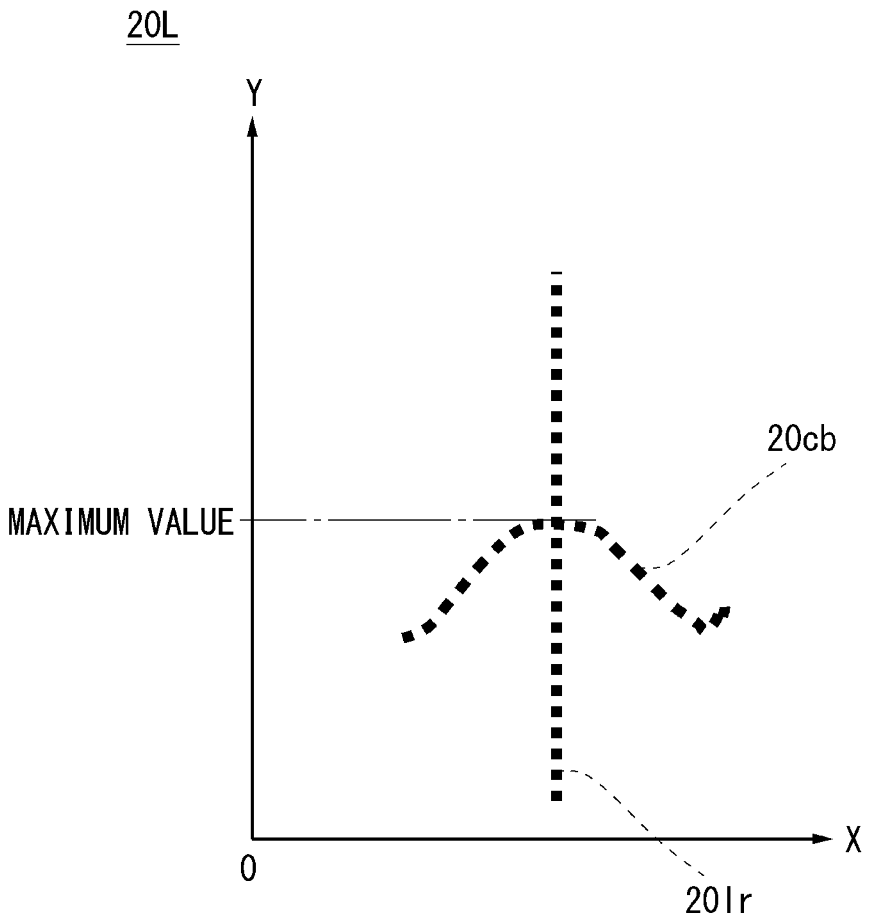
FIG. 19 is a diagram illustrating an example of a division line determined by the information processing apparatus in the display system according to the present disclosure.
Figure 20:
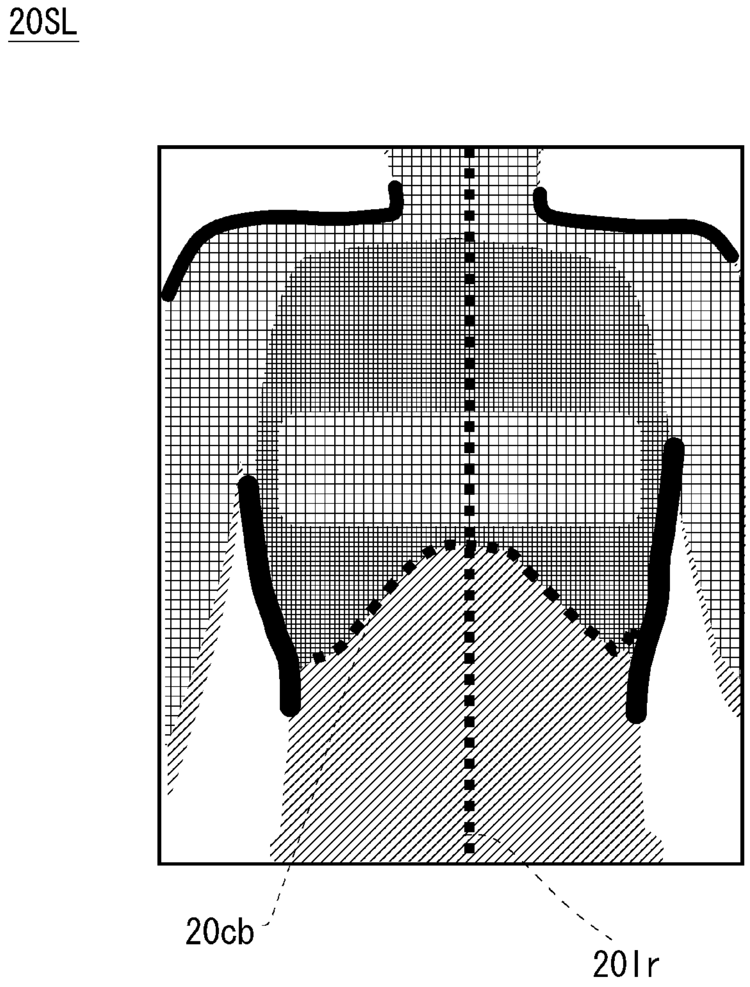
FIG. 20 is a diagram illustrating an example of a division result image generated by the information processing apparatus in the display system according to the present disclosure.

Next, with reference to FIGS. 16 to 20, an example of the chest and abdominal division processing and the left-right division processing using the standard deviation image 20KP will be explained. FIG. 16 is a flowchart for explaining an example of a chest and abdominal division processing and a left-right division processing in the display system 100 according to the present disclosure. FIG. 17 is a schematic diagram illustrating an example of a standard deviation image calculated from the distance image in FIG. 6 by the information processing apparatus 10 according to the present disclosure. FIG. 18 is a graph illustrating an example of a differential value calculated for a certain pixel column in the standard deviation image in FIG. 17 by the information processing apparatus 10 according to the present disclosure. FIG. 19 is a diagram illustrating an example of a dividing line determined by the information processing apparatus 10 according to the present disclosure. FIG. 20 is a diagram illustrating an example of a division result image generated by the information processing apparatus 10 according to the present disclosure.

As described above, the chest and abdominal division processing and the left-right division processing in the display system 100 are not limited to examples to be described below. Herein, for example, an example will be given in which a part of the joint position data are data acquired by analyzing a standard deviation image generated from a distance image series. However, the joint position data may be acquired by the imaging device 20, in other words, the joint position data may be data acquired independently of the distance image data.

First, in the information processing apparatus 10, the standard deviation image calculation unit 13 pre-processes the distance image data with respect to the distance image series, based on the joint key point. Herein, the preprocessing may refer to processing in which an unnecessary region is deleted from the distance image series and the image is rotated in such a way as to be at a normal position when the image is not at a normal position. The unnecessary region may refer to a region that is not required for processing in future, and may refer to, for example, a region above the neck, a region on an end side of the hand, a region below the waist, or the like. Further, the above-described rotation refers to processing of adjusting the direction and the position of the intersection line of each plane with respect to the sagittal plane, the frontal plane, and the transverse plane of the subject 90 to a positive position in such a way as to be suitable for the processing, based on the joint key point. Note that the preprocessing may include processing such as deletion of a region and deformation of an image other than rotation of the image.

By such preprocessing, it is possible to leave, for example, data of a region as indicated by the distance image 20D in FIG. 6 for each distance image of the distance image series being input in step S11. Hereinafter, for the sake of convenience, an example in which the distance image series of the region indicated by the distance image 20D is a processing target will be described.

Next, the standard deviation image calculation unit 13 calculates a standard deviation for the distance image data after the preprocessing, and generates a standard deviation image. This generation processing is the processing of step S12 in FIG. 5. In step S12, the standard deviation image calculation unit 13 calculates the standard deviation of the distance values existing in time series for each pixel of the time-series distance image 20D, and generates a standard deviation image in which the standard deviation value is arranged at the position of the original pixel. The distance image at one time indicated by the distance image series can be, for example, the distance image 20D illustrated in FIG. 6, and the standard deviation image is one image per distance image series, such as a standard deviation image 20S illustrated in FIG. 17. In the standard deviation image 20S, the standard deviation image 20KP in FIG. 7 and the generated standard deviation image are the same. In FIG. 17, as in FIG. 7, the vertical axis represents a row of pixels (in units of pixels) and the horizontal axis represents a column of pixels (in units of pixels).

In the standard deviation image 20S, it can be seen that a region where there is a lot of movements during the breathing exercise of the subject 90 is expressed darkly. In the standard deviation image 20S, for example, it can be seen that both shoulders move well and the flank portion (solar plexus) is moving further, and an area around the abdomen moves more than both arms and an area around the chest moves more than the area around the abdomen.

Next, the division unit 15 generates, from the standard deviation image 20S, an intersection direction differential image that is an image indicating a differential value in a direction of the intersection line between the sagittal plane and the frontal plane of the subject 90, and calculates a local minimum value and a local maximum value of the differential values of each column (step S21). The differential value in the direction of the intersection line refers to a differential value in a direction parallel to the intersection line. The direction of the intersection line may be referred to as a height direction of the subject or a vertical direction. Hereinafter, for convenience, the perpendicular direction will be explained as a Y-axis direction.

The height direction of the subject 90 can be determined in advance as a predetermined direction indicating the height direction of the subject on the distance image or the standard deviation image, but for example, joint position data acquired by measuring a position of a joint of the subject can be input and determined based on the position of the joint. In the former case, measurement may be performed in a state in which the subject is arranged in a predetermined posture and at a predetermined position. In the latter case, the height direction of the subject can be determined based on a plurality of key-point joint positions indicating the position and posture of the subject among the joint positions of the subject.

In short, in the present example embodiment, the "direction" such as the direction of the intersection line between the sagittal plane and the frontal plane may already match the direction of the subject in the time-series distance image data to be input, but may not match the direction of the subject. In the latter case, for example, the joint position can be used as a matching operation, as described above.

The intersection direction differential image (Y-axis direction differential image) generated here will be explained. For example, when a differential value in the Y-axis direction is calculated for a certain pixel column 20*c* in the Y-axis direction of the standard deviation image 20S, the differential value is illustrated by a graph 20Gc in FIG. 18, for example. In the graph 20Gc, the vertical axis represents a row of pixels, the horizontal axis represents a differential value, and points indicated by black circles each represent a local maximum point and points indicated by black squares each represent a local minimum point. As described above, in step S21, in order to generate the intersection direction differential image, processing of acquiring a differential value for each pixel is first performed.

The processing of step S21 is pertinent to an example of a part of processing of the chest and abdominal division processing. In other words, the chest and abdominal division processing may include processing of detecting a local minimum value and a local maximum value for each of the pixel columns in the Y-axis direction with respect to the intersection direction differential image.

Next, as a part of the chest and abdominal division processing, the division unit 15 extracts, on the intersection direction differential image, a region having the maximum area from among a region a pixel whose differential value is a local minimum value exists and a region in which a pixel whose differential value is a local maximum exists, in which the area is the maximum (step S22).

The region in which the local minimum value and the local maximum value exist refers to a region represented by a pixel group indicating the local minimum value and the local maximum value on the intersection direction differential image, i.e., a region represented by a pixel group in which the local minimum value and the local maximum value are plotted on the intersection direction differential image. In a boundary region between the chest portion 92 and the abdomen portion 94 or the like, a plurality of pixels are connected to at least a part of the pixel group.

Therefore, in step S22, substantially, the region of the maximum area is extracted from among the region where the pixels whose differential value is a local maximum value are connected and the region where the pixels whose differential value is a local minimum value are connected, on the Y-axis direction differential image. By the extraction processing in step S22, for example, in a graph 20L illustrated in FIG. 19, a region represented by a chest and abdominal dividing line as indicated by a broken line 20*cb* is extracted. In FIG. 19, the vertical axis is a Y-axis and represents a row of pixels, and the horizontal axis represents a column of pixels, which is an X-axis. The chest and abdominal dividing line that is the broken line 20*cb* roughly is equivalent to a line below the rib, a result based on anatomical knowledge is acquired.

In step S22, the division unit 15 further sets a region on the standard deviation image, which is associated to the extracted result, as a boundary region for dividing the chest region and the abdominal region. This boundary region may be a boundary line represented by a thickness of one pixel as illustrated by the broken line 20*cb* in the graph 20L illustrated in FIG. 19, but may be represented by a thickness of a plurality of pixels. As described above, the information processing apparatus 10 can be configured to identify the region of the chest portion 92 and the region of the abdomen portion 94 of the subject 90 by using the time-series distance image data.

Next, the division unit 15 executes the following processing as an example of the left-right dividing processing described above (step S23). In step S23, as the joint position data, data whose reference point is a point closest to a head side of the boundary region are input, and both the chest region and the abdominal region in the standard deviation image 20S are divided into a left-side region and a right-side region by a straight line passing through the reference point and parallel to the intersection line.

The left and right dividing line to be divided into the left-side region and the right-side region is a line indicated by a broken line 20*lr* in FIG. 19. It can be seen that the broken line 20*lr* is a straight line passing through the reference point and extending in a perpendicular direction with the position of the maximum value in the boundary region indicated by the broken line 20*cb* as a reference point. Herein, since the joint key point is used by the preprocessing, it can be said that the joint key point being input in step S11 is also used for the determination of the perpendicular direction here.

In the processing up to step S23, the chest and abdominal division processing and the left-right division processing are completed. As a result, the generated division result image is similar to an image 20SL illustrated in FIG. 20. In the image 20SL, it can be seen that the left and right dividing line 20*lr* and the chest and abdominal dividing line 20*cb* as illustrated in the image 30SL in FIG. 9 are included. By the division processing as described above, it is possible to perform the region division based on the anatomical knowledge of the subject 90.

In a case where the result of the chest and abdominal division processing is referred to in the left-right division processing as in this example, it is assumed that the processing for detecting the joint is basically performed by the information processing apparatus 10 side instead of the imaging device 20 side. However, even in a case of adopting the left-right division processing as in step S23, the chest and abdominal division processing is not limited to the processing using the local maximum value and the local minimum value described above. The chest and abdominal division processing may be any processing as long as it can acquire a boundary region that serves as a boundary for dividing a region on the standard deviation image into a chest region and an abdominal region by image analysis of the distance image series. Further, as described above, the left-right division processing may be divided as a straight line passing through the reference point and extending in the perpendicular direction, based on a predetermined reference point indicated by the joint key point being input in step S11, without using the image analysis result of the distance image sequence.

As described above, in the division processing example described with reference to FIGS. 16 to 20, the standard deviation image indicating the motion of the subject can be divided into the chest region and the abdominal region along the anatomical knowledge, and can be divided into the left region and the right region.

In particular, by performing the left-right division processing using the division result of the chest region and the abdominal region, the standard deviation image can be divided into the left region and the right region according to anatomical knowledge. This effect is supplementarily described. For example, in motor organ disorders such as low back pain, abnormal respiratory patterns occur, and therefore, exercise examination and exercise evaluation of the chest and abdomen during respiratory exercise are important. In addition, since these tests and evaluations by experts are generic, objective and quantitative inspection and evaluation techniques are required. In the example of the division processing described here, the standard deviation image can be divided into the left region and the right region as well as the chest region and the abdominal region according to anatomical knowledge, so that it can be said that the accuracy of such inspection and evaluation can be improved.

That is, with such a configuration, it is possible to identify the region between the thoracic region and the abdominal region along the anatomical knowledge, and identify the region between the left region and the right region, thereby achieving the following effects. That is, with such a configuration, for example, the respiratory feature amounts of the right chest, the left chest, the right abdomen, and the left abdomen can be accurately calculated for each region, and the respiratory feature amounts for the motor organ disorder can be correctly defined. With such a configuration, it is possible to improve the accuracy of the examination for capturing the movement of the right chest, the left chest, the right abdomen, and the left abdomen, and to improve the accuracy of the estimation of the respiratory state of the subject. As a result, the accuracy of the evaluation of the respiratory motion can be improved, and the accuracy of the guidance using the evaluation can also be improved, and effective guidance becomes possible.

Other Application Examples in This Embodiment

In the present example embodiment, an example in which the supine position is adopted as the posture of the subject at the time of acquiring the distance image data has been described. However, as described in the first example embodiment, the present invention is not limited thereto, and may be performed not only in the supine position, the sitting position, the standing position, the knee standing position, the supine position, and the leg raising position. However, the installation location of the imaging device 20, the various image processing described above, and the like may be changed as appropriate in accordance with the posture. The distance image data may be acquired from the front or back of the subject in accordance with the posture of the subject, but the posture that can be acquired from the front does not need to restrict the breathing of the subject.

Further, the display system 100 may include a plurality of imaging devices 20 as described above, and the subject 90 may be captured using the plurality of imaging devices 20. With this configuration, since the subject 90 can be photographed from a plurality of viewpoints, the distance image data can be generated from the data of both viewpoints. Further, by using the plurality of imaging devices 20, it is possible to suppress the occurrence of a blind spot of the subject 90 at the time of photographing, it is possible to perform the detection of the displacement amount or the like which can be used for calculation of other respiratory feature amount with high accuracy, it is possible to calculate the respiratory feature amount with high accuracy.

Further, the display system 100 may be realized by a device in which two or more of the imaging device 20, the display device 30, and the information processing apparatus 10 are integrally configured. For example, the subject 90 may perform respiration training or a respiration test using one device (e.g., a smartphone) including the imaging device 20, the display device 30, and the information processing apparatus 10. This allows breathing training and breathing tests to be performed without special equipment. For example, the subject 90 can perform breathing training and breathing tests at home or the like without hesitation.

Further, as described above, for example, the display system 100 may be configured such that a sensor for detecting a ratio of carbon dioxide is provided in a nose or the like of the subject 90, and an exhalation analysis is performed based on a detection result of the sensor. With such a configuration, for example, it can be used to extract time-series distance image data for calculating a standard deviation image, that is, it can be used to specify a period of use data.

Further, by using this sensor, it is possible to easily classify time-series distance image data into expiratory phase data and inspiratory phase data from the detection result of this sensor. Therefore, since the expiratory phase and the inspiratory phase in the time-series distance image data can be specified by such a configuration, the calculation of the standard deviation image and the calculation of the respiratory feature amount in the expiratory phase, the calculation of the standard deviation image in the inspiratory phase, and the calculation of the respiratory feature amount become possible. That is, with such a configuration, both the respiratory feature amount for the expiratory phase and the respiratory feature amount for the inspiratory phase can be calculated, and output such as display can be performed.

Third Example Embodiment

Figure 21:
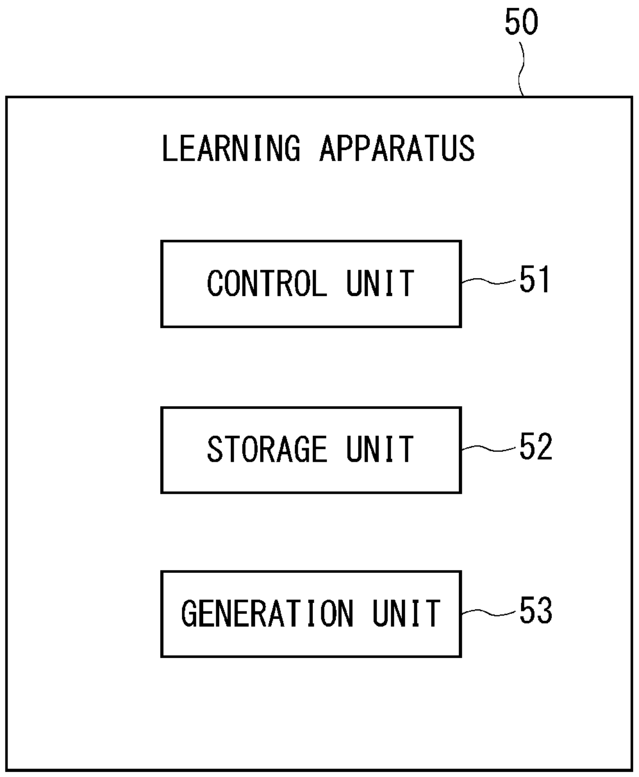
FIG. 21 is a block diagram illustrating a configuration example of a learning apparatus according to the present disclosure.

Although the third example embodiment will be mainly described with reference to FIG. 21, various examples described in the first and second example embodiments can be applied. FIG. 21 is a block diagram illustrating an example of a configuration of a learning apparatus according to the present disclosure.

As illustrated in FIG. 21, the learning apparatus 50 according to the present example embodiment may include a control unit 51, a storage unit 52, and a generation unit 53. The control unit 51 may include, for example, a processor such as a CPU or a GPU, and may include a program for controlling the entire learning apparatus 50. The control unit 51 has a function as an arithmetic device that performs control processing, arithmetic processing, and the like, and controls the storage unit 52 and the generation unit 53.

The storage unit 52 may be configured by a storage device. The storage unit 52 stores a set of data (learning data set) including the respiratory feature amount calculated by the information processing apparatus 1 or the information processing apparatus 10 and an evaluation label that evaluates the respiratory function of the subject corresponding to the respiratory feature amount. The learning data set is as described above with reference to the description of the evaluation unit 17 and FIGS. 9 to 11.

Here, the evaluation label may include at least one of the first evaluation label and the second evaluation label, as described with respect to the evaluation unit 17 in the second example embodiment. The first evaluation label is a label that evaluates the respiratory function related to the movement of the subject 90 in a direction perpendicular to the frontal plane, and the second evaluation label is a label that evaluates the respiratory function related to the movement of the subject 90 in a direction perpendicular to the sagittal plane.

Further, the storage unit 52 stores an untrained model. However, the non-learning model may be a learning model that has been machine-learned by a past learning data set as long as it is a learning model that is not currently operated. Regardless of the non-learning model, the algorithm of the learned model, or the like, various existing machine learning models as exemplified in the description of the evaluation unit 17 can be applied.

The generation unit 53 generates a learned model in which the learning data set is input to the non-learning model, machine learning is performed, and the respiratory feature amount is input to output an evaluation label. The generated learned model can be stored in the evaluation unit 17 or the storage unit 18 of the information processing apparatus 10. As a result, the evaluation as described in the second example embodiment can be performed.

Further, although the description has been made on the assumption that the respiratory feature amount included in the learning data set is the respiratory feature amount calculated by the information processing apparatus 1 or the information processing apparatus 10, the present invention is not limited to this. The respiratory feature amount included in the learning data set may be any respiratory feature amount calculated based on the standard deviation image indicating the standard deviation of the value for each pixel in the distance image indicated by the time-series distance image data obtained by measuring the distance from the subject during the respiratory exercise. That is, the respiratory feature amount included in the learning data set may be a respiratory feature amount calculated without using the division position data, unlike the respiratory feature amount calculated by the information processing apparatus 1 or the information processing apparatus 10.

Modified Example

The present disclosure is not limited to the above-described example embodiments, and can be appropriately modified without departing from the scope and spirit. For example, one or more of the above-described components of each device may be omitted as appropriate. Also, for example, one or more of the steps of the above-described flow diagrams may be omitted as appropriate. Also, the order of one or more of the steps in the flow diagrams described above may be changed as appropriate.

Further, the information processing apparatus 10 may generate a respiration characteristic amount acquired by processing of a respiration waveform or a light load based on data acquired during the respiration training or the respiration examination, display the result on the display device 30 in real time, and update the result over time. As the non-real-time processing, as described in Embodiments 1 and 2, the respiratory feature amount or the like acquired by using the stored time-series distance image data or the like can be output to the display device or the like.

In addition, in a device such as a smartphone, skeleton data may not be acquired in some cases. In this case, the subject may perform an operation to designate a joint key point in the photographed image of the subject.

Figure 22:
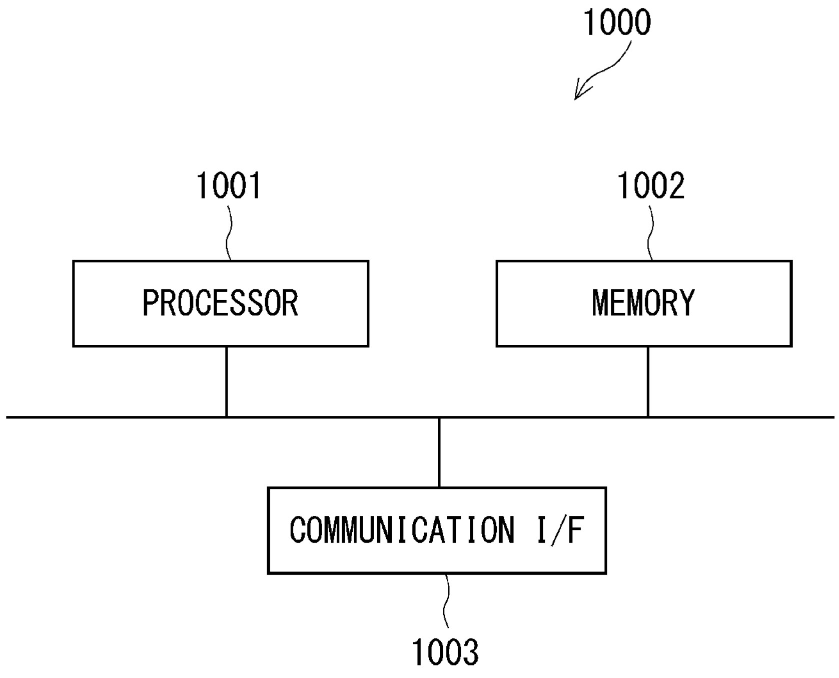
FIG. 22 is a diagram illustrating an example of a hardware configuration included in the apparatus according to the present disclosure.

Each of the apparatuses according to Embodiments 1 to 3 can have the following hardware configuration. FIG. 22 is a diagram illustrating an example of a hardware configuration included in the apparatus according to the present disclosure.

The apparatus 1000 illustrated in FIG. 22 includes a processor 1001, a memory 1002, and a communication interface 1003. The function of each device can be realized by the processor 1001 reading a program stored in the memory 1002 and executing the program in cooperation with the communication interface 1003.

The program includes instructions (or software codes) that, when loaded into a computer, cause the computer to perform one or more of the functions described in the example embodiments. The program may be stored in a non-transitory computer readable medium or a tangible storage medium. By way of example, and not limitation, non-transitory computer readable media or tangible storage media can include a random-access memory (RAM), a read-only memory (ROM), a flash memory, a solid-state drive (SSD) or other memory technologies, CD-ROM, digital versatile disc (DVD), Blu-ray disc or other optical disc storage, magnetic cassettes, magnetic tape, magnetic disk storage or other magnetic storage devices. The program may be transmitted on a transitory computer readable medium or a communication medium. By way of example, and not limitation, transitory computer readable media or communication media can include electrical, optical, acoustical, or other form of propagated signals.

The first to third example embodiments can be combined as desirable by one of ordinary skill in the art.

Each of the drawings or figures is merely an example to illustrate one or more example embodiments. Each figure may not be associated with only one particular example embodiment, but may be associated with one or more other example embodiments. As those of ordinary skill in the art will understand, various features or steps described with reference to any one of the figures can be combined with features or steps illustrated in one or more other figures, for example, to produce example embodiments that are not explicitly illustrated or described. Not all of the features or steps illustrated in any one of the figures to describe an example embodiment are necessarily essential, and some features or steps may be omitted. The order of the steps described in any of the figures may be changed as appropriate.

The whole or part of the exemplary example embodiments disclosed above can be described as, but not limited to, the following supplementary notes.

Supplementary Note 1

An information processing apparatus including:

an input unit configured to input time-series distance image data acquired by measuring a distance from a subject during a breathing exercise and division position data indicating a position at which a chest region and an abdominal region of the subject are divided in the time-series distance image data;

a standard deviation calculation unit configured to calculate a standard deviation image indicating a standard deviation of values for each pixel in a distance image indicated by the time-series distance image data; and a feature amount calculation unit configured to calculate a respiratory feature amount indicating a feature of breathing of the subject, based on a divided standard deviation image acquired by dividing the standard deviation image for each divided region being divided at a position indicated by the division position data.

Supplementary Note 2

The information processing apparatus according to supplementary note 1, wherein the feature amount calculation unit calculates an average value of standard deviations indicated by the divided standard deviation image for each of the divided regions as one of the respiratory feature amounts.

Supplementary Note 3

The information processing apparatus according to supplementary note 1, wherein the feature amount calculation unit calculates synchrony of the divided standard deviation image between the divided regions as one of the respiratory feature amounts.

Supplementary Note 4

The information processing apparatus according to any one of supplementary notes 1 to 3, wherein the feature amount calculation unit extracts a region having a standard deviation of a predetermined value or more with respect to the standard deviation image, and calculates the respiratory feature amount, based on the extracted standard deviation image.

Supplementary Note 5

The information processing apparatus according to any one of supplementary notes 1 to 4, wherein the feature amount calculation unit calculates, an expansion area of a flank region as one of the respiratory feature amounts, the expansion area being a difference in an area from an expansion state to a contraction state, the flank region being a region capable of expanding and contracting in a direction of an intersection line between a frontal plane and a transverse plane of the subject in both the chest region and the abdominal region.

Supplementary Note 6

The information processing apparatus according to any one of supplementary notes 1 to 5, wherein the feature amount calculation unit calculates, as one of the respiratory feature amounts, an average value of standard deviations indicated by the standard deviation image for a flank region that is a region capable of expanding and contracting in a direction of an intersection line between a frontal plane and a transverse plane of the subject in both the chest region and the abdominal region.

Supplementary Note 7

The information processing apparatus according to any one of supplementary notes 1 to 6, wherein the division position data include data indicating a position at which a left-side region and a right-side region of the subject are divided.

Supplementary Note 8

The information processing apparatus according to any one of supplementary notes 1 to 7, wherein the division position data include data indicating a position at which the chest region and a shoulder region of the subject are divided.

Supplementary Note 9

The information processing apparatus according to any one of supplementary notes 1 to 6, wherein the division position data include data indicating a position at which the chest region and a shoulder region of the subject are divided, and a position at which a left-side region and a right-side region of the subject are divided for the chest region and the abdominal region.

Supplementary Note 10

The information processing apparatus according to supplementary note 8 or 9, wherein the feature amount calculation unit calculates, as one of the respiratory feature amounts, an expansion area of a shoulder expansion and contraction region, the expansion area being a difference in an area from an expansion state to a contraction state, the shoulder expansion and contraction region being a region capable of expanding and contracting in a direction of an intersection line between a frontal plane and a sagittal plane of the subject in the shoulder region.

Supplementary Note 11

The information processing apparatus according to any one of supplementary notes 1 to 10, further including an output unit configured to output the respiratory feature amount.

Supplementary Note 12

The information processing apparatus according to supplementary note 11, wherein the output unit outputs a history of the respiratory feature amount.

Supplementary Note 13

The information processing apparatus according to supplementary note 11 or 12, wherein the output unit outputs a message to the subject associated with the respiratory feature amount in advance.

Supplementary Note 14

The information processing apparatus according to any one of supplementary notes 1 to 13, wherein the time-series distance image data are data measured for one or a plurality of breathing cycles of the subject.

Supplementary Note 15

The information processing apparatus according to any one of supplementary notes 1 to 14, wherein the time-series distance image data are data measured while the subject is breathing deep.

Supplementary Note 16

The information processing apparatus according to any one of supplementary notes 1 to 15, further including an evaluation unit configured to acquire an evaluation label by inputting the respiratory feature amount to a learned model, the evaluation label evaluating a breathing function of the subject associated to the respiratory feature amount, the learned model being machine-learned in such a way as to receive the respiratory feature amount and output the evaluation label.

Supplementary Note 17

The information processing apparatus according to supplementary note 16, wherein the evaluation label includes at least one of a first evaluation label that evaluates a breathing function related to a movement in a direction perpendicular to a frontal plane of the subject, and a second evaluation label that evaluates a breathing function related to a movement in a direction perpendicular to a sagittal plane of the subject.

Supplementary Note 18

A learning apparatus including:

a storage unit configured to store a set of data including the respiratory feature amount calculated by the information processing apparatus according to any one of supplementary notes 1 to 15 and an evaluation label evaluating a breathing function of the subject associated to the respiratory feature amount; and a generation unit configured to input the set of data into a learning model, perform machine learning, and generate a learned model that inputs the respiratory feature amount and outputs the evaluation label.

Supplementary Note 19

The learning apparatus further including:

a storage unit configured to memorize a set of data containing a respiratory feature amount indicating a feature of breathing of a subject during a breathing exercise and an evaluation label evaluating a breathing function of the subject associated to the respiratory feature amount, the respiratory feature amount being calculated based on a standard deviation image indicating a standard deviation of values for each pixel in a distance image indicated by time series distance image data acquired by measuring a distance from the subject; and a generation unit configured to input a set of the data into a learning model, perform machine learning, generate a learned model that inputs the respiratory feature amount and outputs the evaluation label.

Supplementary Note 20

The learning apparatus according to supplementary note 18 or 19, wherein the evaluation label includes at least one of a first evaluation label evaluating a breathing function related to a movement of the subject in a direction perpendicular to a frontal plane, and a second evaluation label evaluating a breathing function related to a movement of the subject in a direction perpendicular to a sagittal plane.

Supplementary Note 21

An information processing method including:

inputting time-series distance image data acquired by measuring a distance from a subject during a breathing exercise and division position data indicating a position at which a chest region and an abdominal region of the subject are divided in the time-series distance image data;

calculating a standard deviation image indicating a standard deviation of values for each pixel in a distance image indicated by the time-series distance image data; and calculating a respiratory feature amount indicating a feature of breathing of the subject, based on a divided standard deviation image acquired by dividing the standard deviation image for each divided region being each divided at a position indicated by the division position data.

Supplementary Note 22

The information processing method according to supplementary note 21, further including calculating, as one of the respiratory feature amounts, an average value of standard deviations indicated by the divided standard deviation image for each of the divided regions.

Supplementary Note 23

The information processing method according to supplementary note 21 or 22, further including calculating, as one of the respiratory feature amounts, a synchrony of the divided standard deviation image between the divided regions.

Supplementary Note 24

The information processing method according to any one of supplementary notes 21 to 23, wherein the calculating the respiratory feature amount includes extracting a region having a standard deviation of a predetermined value or more with respect to the standard deviation image and calculating the respiratory feature amount, based on the extracted standard deviation image.

Supplementary Note 25

The information processing method according to any one of supplementary notes 21 to 24, further including calculating, as one of the respiratory characteristic amounts, an expansion area of a flank region, the expansion area being a difference in an area from an expansion state to a contraction state, the flank region being a region capable of expanding and contracting in a direction of an intersection line between a frontal plane and a transverse plane of the subject in both the chest region and the abdominal region.

Supplementary Note 26

The information processing method according to any one of supplementary notes 21 to 25, further including calculating, as one of the respiratory feature amounts, an average value of standard deviations indicated by the standard deviation image for a flank region being a region capable of expanding and contracting in a direction of an intersection line between a frontal plane and a transverse plane of the subject in both the chest region and the abdominal region.

Supplementary Note 27

The information processing method according to any one of supplementary notes 21 to 26, wherein the division position data include data indicating a position at which a left-side region and a right-side region of the subject are divided.

Supplementary Note 28

The information processing method according to any one of supplementary notes 21 to 27, wherein the division position data include data indicating a position at which the chest region and a shoulder region of the subject are divided.

Supplementary note 29

The information processing method according to any one of supplementary notes 21 to 26, wherein the division position data include data indicating a position at which the chest region and a shoulder region of the subject are divided and a position at which a left-side region and a right-side region of the subject are divided for the chest region and the abdominal region.

Supplementary Note 30

The information processing method according to supplementary note 28 or 29, further including calculating, as one of the respiratory feature amounts, an expansion area of a shoulder expansion and contraction region, the expansion area being a difference in an area from an expansion state to a contraction state, the shoulder expansion and contraction region being a region capable of expanding and contracting in a direction of an intersection line between a frontal plane and a sagittal plane of the subject in the shoulder region.

Supplementary Note 31

The information processing method according to any one of supplementary notes 21 to 30, further including executing output processing of outputting the respiratory feature amount.

Supplementary Note 32

The information processing method according to supplementary note 31, wherein the output processing includes processing of outputting a history of the respiratory feature amount.

Supplementary Note 33

The information processing method according to supplementary note 31 or 32, wherein the output processing includes processing of outputting a message to the subject associated with the respiratory feature amount in advance.

Supplementary Note 34

The information processing method according to any one of supplementary notes 21 to 33, wherein the time-series distance image data are data measured for one or a plurality of breathing cycles of the subject.

Supplementary Note 35

The information processing method according to any one of supplementary notes 21 to 34, wherein the time-series distance image data are data measured while the subject is breathing deep.

Supplementary Note 36

The information processing method according to any one of supplementary notes 21 to 35, further including acquiring an evaluation label by inputting the respiratory feature amount to a learned model, the evaluation label evaluating a breathing function of the subject associated to the respiratory feature amount, the learned model being machine-learned in such a way as to receive the respiratory feature amount and output the evaluation label.

Supplementary Note 37

The information processing method according to supplementary note 36, wherein the evaluation label includes at least one of a first evaluation label that evaluates a breathing function related to a movement of the subject in a direction perpendicular to a frontal plane, and a second evaluation label that evaluates a breathing function related to a movement of the subject in a direction perpendicular to a sagittal plane.

Supplementary Note 38

A learning method including:

storing a set of data including the respiratory feature amount calculated by the information processing method according to any one of supplementary notes 21 to 35 and an evaluation label evaluating a breathing function of the subject associated to the respiratory feature amount;

inputting the set of the data into a learning model, performing machine learning, and generating a learned model that inputs the respiratory feature amount and outputs the evaluation label.

Supplementary Note 39

A learning method including:

storing a set of data including a respiratory feature amount indicating a feature of breathing of a subject during a breathing exercise and an evaluation label evaluating a breathing function of the subject associated to the respiratory feature amount, the respiratory feature amount being calculated based on a standard deviation image indicating a standard deviation of values for each pixel in a distance image indicated by time-series distance image data acquired by measuring a distance from the subject; and inputting the set of the data into a learning model, performing machine learning, and generating a learned model that inputs the respiratory feature amount and outputs the evaluation label.

Supplementary Note 40

The learning method according to supplementary note 38 or 39, wherein the evaluation label includes at least one of a first evaluation label evaluating a breathing function related to a movement of the subject in a direction perpendicular to a frontal plane, and a second evaluation label evaluating a breathing function related to a movement of the subject in a direction perpendicular to a sagittal plane.

Supplementary Note 41

A program causing a computer to execute information processing of:

inputting time-series distance image data acquired by measuring a distance from a subject during a breathing exercise and division position data indicating a position at which a chest region and an abdominal region of the subject are divided in the time-series distance image data;

calculating a standard deviation image indicating a standard deviation of values for each pixel in a distance image indicated by the time-series distance image data; and calculating a respiratory feature amount indicating a feature of breathing of the subject, based on a divided standard deviation image acquired by dividing the standard deviation image for each divided region being divided at a position indicated by the division position data.

Supplementary Note 42

The program according to supplementary note 41, further causing a computer to execute processing of calculating, as one of the respiratory feature amounts, an average value of standard deviations indicated by the divided standard deviation image for each of the divided regions.

Supplementary Note 43

The program according to supplementary note 41 or 42, further causing a computer to execute processing of calculating, as one of the respiratory feature amounts, a synchrony of the divided standard deviation image between the divided regions.

Supplementary Note 44

The program according to any one of supplementary notes 41 to 43, wherein the calculating the respiratory feature amount includes extracting a region having a standard deviation of a predetermined value or more with respect to the standard deviation image, and calculating the respiratory feature amount, based on the extracted standard deviation image.

Supplementary Note 45

The program according to any one of supplementary notes 41 to 44, further causing a computer to execute processing of calculating, as one of the respiratory feature amounts, an expansion area of a flank region, the expansion area being a difference in an area from an expansion state to a contraction state, the flank region being a region capable of expanding and contracting in a direction of an intersection line between a frontal plane and a transverse plane of the subject in both the chest region and the abdominal region.

Supplementary Note 46

The program according to any one of supplementary notes 41 to 45, further causing a computer to execute processing of calculating, as one of the respiratory feature amounts, an average value of standard deviations indicated by the standard deviation image for a flank region being a region capable of expanding and contracting in a direction of an intersection line between a frontal plane and a transverse plane of the subject in both the chest region and the abdominal region.

Supplementary Note 47

The program according to any one of supplementary notes 41 to 46, wherein the division position data include data indicating a position at which a left-side region and a right-side region of the subject are divided.

Supplementary Note 48

The program according to any one of supplementary notes 41 to 47, wherein the division position data include data indicating a position at which the chest region and a shoulder region of the subject are divided.

Supplementary Note 49

The program according to any one of supplementary notes 41 to 46, wherein the division position data include data indicating a position at which the chest region and a shoulder region of the subject are divided, and a position at which a left-side region and a right-side region of the subject are divided for the chest region and the abdominal region.

Supplementary Note 50

The program according to supplementary note 48 or 49, further causing a computer to execute processing of calculating, as one of the respiratory feature amounts, an expansion area of a shoulder expansion and contraction region, the expansion area being a difference in an area from an expansion state to a contraction state, the shoulder expansion and contraction region being a region capable of expanding and contracting in a direction of an intersection line between a frontal plane and a sagittal plane of the subject in the shoulder region.

Supplementary Note 51

The program according to any one of supplementary notes 41 to 50, wherein the information processing includes output processing of outputting the respiratory feature amount.

Supplementary Note 52

The program according to supplementary note 51, wherein the output processing includes processing of outputting a history of the respiratory feature amount.

Supplementary Note 53

The program according to supplementary note 51 or 52, wherein the output processing includes processing of outputting a message to the subject associated with the respiratory feature amount in advance.

Supplementary Note 54

The program according to any one of supplementary notes 41 to 53, wherein the time-series distance image data are data measured for one or a plurality of breathing cycles of the subject.

Supplementary Note 55

The program according to any one of supplementary notes 41 to 54, wherein the time-series distance image data are data measured while the subject is breathing deep.

Supplementary Note 56

The program according to any one of supplementary notes 41 to 55, wherein the information processing includes processing of acquiring an evaluation label that evaluates a breathing function of the subject associated to the respiratory feature amount, by inputting the respiratory feature amount to a learned model that is machine-learned in such a way as to receive the respiratory feature amount and output the evaluation label.

Supplementary Note 57

The program according to supplementary note 56, wherein the evaluation label includes at least one of a first evaluation label that evaluates a breathing function related to a movement of the subject in a direction perpendicular to a frontal plane, and a second evaluation label that evaluates a breathing function related to a movement of the subject in a direction perpendicular to a sagittal plane.

Supplementary Note 58

A program causing a computer to execute learning processing of:

storing a set of data including the respiratory feature amount calculated by the program according to any one of supplementary notes 41 to 55 and an evaluation label evaluating a breathing function of the subject associated to the respiratory feature amount; and inputting the set of the data into a learning model, performing machine learning, and generating a learned model that inputs the respiratory feature amount and outputs the evaluation label.

Supplementary Note 59

A program causing a computer to execute learning processing of:

storing a set of data including a respiratory feature amount indicating a feature of breathing of the subject and an evaluation label evaluating a breathing function of the subject associated to the respiratory feature amount, the respiratory feature amount being calculated based on a standard deviation image indicating a standard deviation of values for each pixel in a distance image indicated by time-series distance image data acquired by measuring a distance from a subject during a breathing exercise; and inputting the set of the data into a learning model, performing machine learning, and generating a learned model that inputs the respiratory feature amount and outputs the evaluation label.

Supplementary Note 60

The program according to supplementary note 58 or 59, wherein the evaluation label includes at least one of a first evaluation label evaluating a breathing function related to a movement of the subject in a direction perpendicular to a frontal plane, and a second evaluation label evaluating a breathing function related to a movement of the subject in a direction perpendicular to a sagittal plane.

According to the present disclosure, it is possible to provide an information processing apparatus, an information processing method, a program, and the like that are capable of calculating a respiratory feature amount necessary for evaluating a breathing motor function of a subject.

While the disclosure has been particularly illustrated and described with reference to example embodiments thereof, the disclosure is not limited to these example embodiments. It will be understood by those of ordinary skill in the art that various changes in form and details may be made therein without departing from the spirit and scope of the present disclosure as defined by the claims.

What is claimed is:

1. An information processing apparatus comprising:

at least one memory storing instructions; and at least one processor configured to execute the instructions to:

obtain, from a three-dimensional sensor, time-series distance image data acquired by measuring a distance from a subject during a breathing exercise and division position data indicating a position at which a chest region and an abdominal region of the subject are divided in the time-series distance image data;

calculate a standard deviation image indicating a standard deviation of values for each pixel in a distance image indicated by the time-series distance image data; and calculate a respiratory feature amount indicating a feature of breathing of the subject, based on a divided standard deviation image acquired by dividing the standard deviation image for each divided region as divided along a boundary indicated by the division position data;

generate, based on the respiratory feature amount, output information indicating guidance for breathing training; and cause the output information to be output.

2. The information processing apparatus according to claim 1, wherein the calculating the respiratory feature amount includes calculating an average value of standard deviations indicated by the divided standard deviation image for each of the divided regions as one of the respiratory feature amounts.

3. The information processing apparatus according to claim 1, wherein the calculating the respiratory feature amount includes calculating a synchrony of the divided standard deviation image between the divided regions as one of the respiratory feature amounts.

4. The information processing apparatus according to claim 1, wherein the calculating the respiratory feature amount includes extracting a region having a standard deviation of a predetermined value or more with respect to the standard deviation image, and calculating the respiratory feature amount, based on the extracted standard deviation image.

5. The information processing apparatus according to claim 1, wherein the calculating the respiratory feature amount includes calculating, as one of the respiratory feature amounts, an expansion area of a flank region, the expansion area is defined as a difference in area between an expansion state and a contraction state, the flank region being a region capable of expanding and contracting in a direction of an intersection line between a frontal plane and a transverse section of the subject in both the chest region and the abdominal region.

6. The information processing apparatus according to claim 1, wherein the calculating the respiratory feature amount includes calculating, as one of the respiratory feature amounts, an average value of standard deviations indicated by the standard deviation image for a flank region that is a region capable of expanding and contracting in a direction of an intersection line between a frontal plane and a transverse plane of the subject in both the chest region and the abdominal region.

7. The information processing apparatus according to claim 1, wherein the division position data includes data indicating a position at which a left-side region and a right-side region of the subject are divided.

8. The information processing apparatus according to claim 1, wherein the division position data include data indicating a position at which the chest region and a shoulder region of the subject are divided.

9. The information processing apparatus according to claim 1, wherein the division position data include data indicating a position at which the chest region and a shoulder region of the subject are divided, and a position at which a left-side region and a right-side region of the subject are divided with respect to the chest region and the abdominal region.

10. The information processing apparatus according to claim 8, wherein the calculating the respiratory feature amount includes calculating, as one of the respiratory feature amounts, an expansion area of a shoulder expansion and contraction region, the expansion area is defined as a difference in area between an expansion state and a contraction state, the shoulder expansion and contraction region being a region capable of expanding and contracting in a direction of an intersection line between a frontal plane and a sagittal plane of the subject in the shoulder region.

11. The information processing apparatus according to claim 1, wherein the at least one processor is configured to execute outputting the respiratory feature amount.

12. The information processing apparatus according to claim 11, wherein the at least one processor is configured to execute outputting a history of the respiratory feature amount.

13. The information processing apparatus according to claim 11, wherein the at least one processor is configured to execute outputting a message to the subject that is previously associated with the respiratory feature amount.

14. The information processing apparatus according to claim 1, wherein the time-series distance image data are data measured for one or a plurality of breathing cycles of the subject.

15. The information processing apparatus according to claim 1, wherein the time-series distance image data are data measured while the subject is breathing deep.

16. The information processing apparatus according to claim 1, wherein the at least one processor is configured to execute acquiring an evaluation label evaluating a breathing function of the subject associated to the respiratory feature amount, by inputting the respiration feature amount to a learned model that is machine-learned in such a way as to receive the respiratory feature amount and output the evaluation label.

17. The information processing apparatus according to claim 16, wherein the evaluation label includes at least one of a first evaluation label that evaluates the breathing function related to a movement of the subject in a direction perpendicular to a frontal plane, and a second evaluation label that evaluates the breathing function related to a movement of the subject in a direction perpendicular to a sagittal plane.

18. A learning apparatus comprising another at least one memory configured to store a set of data and generation instructions, the set of the data including the respiratory feature amount calculated by the information processing apparatus according to claim 1 and an evaluation label that evaluates a breathing function of the subject associated to the respiratory feature amount, and another at least one processor configured to execute the generation instructions to:

input the set of the data into a learning model; perform machine learning; and generate a learned model that inputs the respiratory feature amount and outputs the evaluation label.

19. An information processing method comprising:

obtain, from a three-dimensional sensor, time-series distance image data acquired by measuring a distance from a subject during a breathing exercise and division position data indicating a position at which a chest region and an abdominal region of the subject are divided in the time-series distance image data;

calculating a standard deviation image indicating a standard deviation of values for each pixel in a distance image indicated by the time-series distance image data;

calculating a respiratory feature amount indicating a feature of breathing of the subject, based on a divided standard deviation image acquired by dividing the standard deviation image for each divided region as divided along a boundary indicated by the division position data;

generating, based on the respiratory feature amount, output information indicating guidance for breathing training; and causing the output information to be output.

20. A non-transitory computer readable medium storing a program that causes a computer to execute information processing of:

obtaining, from a three-dimensional sensor, time-series distance image data acquired by measuring a distance from a subject during a breathing exercise and division position data indicating a position at which a chest region and an abdominal region of the subject are divided in the time-series distance image data;

calculating a standard deviation image indicating a standard deviation of values for each pixel in a distance image indicated by the time-series distance image data;

calculating a respiratory feature amount indicating a feature of breathing of the subject, based on a division standard deviation image acquired by dividing the standard deviation image for each divided region as divided along a boundary indicated by the division position data;

generating, based on the respiratory feature amount, output information indicating guidance for breathing training; and causing the output information to be output.

* * * * *